US009527208B2

(12) United States Patent
Merana et al.

(10) Patent No.: US 9,527,208 B2
(45) Date of Patent: *Dec. 27, 2016

(54) SYSTEM, METHOD, AND APPARATUS FOR REFURBISHMENT OF ROBOTICALLY CONTROLLED DEVICES

(71) Applicant: F21, LLC, St. Petersburg, FL (US)

(72) Inventors: Paul Merana, Tallahassee, FL (US); Mathew McGowan, St. Petersburg, FL (US)

(73) Assignee: F21, LLC, St. Petersburg, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/566,144

(22) Filed: Dec. 10, 2014

(65) Prior Publication Data

US 2016/0167225 A1 Jun. 16, 2016

(51) Int. Cl.
*B25J 9/16* (2006.01)

(52) U.S. Cl.
CPC ............. *B25J 9/16* (2013.01); *Y10S 901/49* (2013.01)

(58) Field of Classification Search
CPC ......... B25J 9/16; Y10S 901/49; Y10S 901/02; A61B 19/2203; A61B 19/44; A61B 2019/2223; A61B 2019/2234; A61B 2019/448; B23P 6/00
See application file for complete search history.

(56) References Cited

U.S. PATENT DOCUMENTS

| 5,624,316 A * | 4/1997 | Roskowski | A63F 13/02 463/41 |
| 9,247,996 B1 * | 2/2016 | Merana | A61B 19/2203 |
| 2007/0005045 A1 * | 1/2007 | Mintz | A61B 19/2203 606/1 |
| 2015/0059511 A1 * | 3/2015 | Mushikami | B25J 17/0283 74/490.06 |
| 2015/0068350 A1 * | 3/2015 | Kirihara | B25J 17/02 74/490.05 |

* cited by examiner

*Primary Examiner* — Rodney Butler
(74) *Attorney, Agent, or Firm* — Larson & Larson, P.A.; Frank Liebenow; Justin P. Miller

(57) ABSTRACT

A device for extending the life of a detachable robotically controlled device that has an electrical interface for communicating between a control system and a robotically controlled device-based circuit mounted within the robotically controlled device includes a circuit that is connected to the electrical interface. The circuit has logic that intercepts requests from the electrical interface such that the logic array recognizes at least one request from the control system and the logic array responds to the at least one request by sending a response to the control system over the electrical interface. At least one other request is forwarded by the logic array to the robotically controlled device-based circuit of which a response from the robotically controlled device-based circuit is received by the logic array and the response is forwarded by the logic array to the control system over the electrical interface.

17 Claims, 18 Drawing Sheets

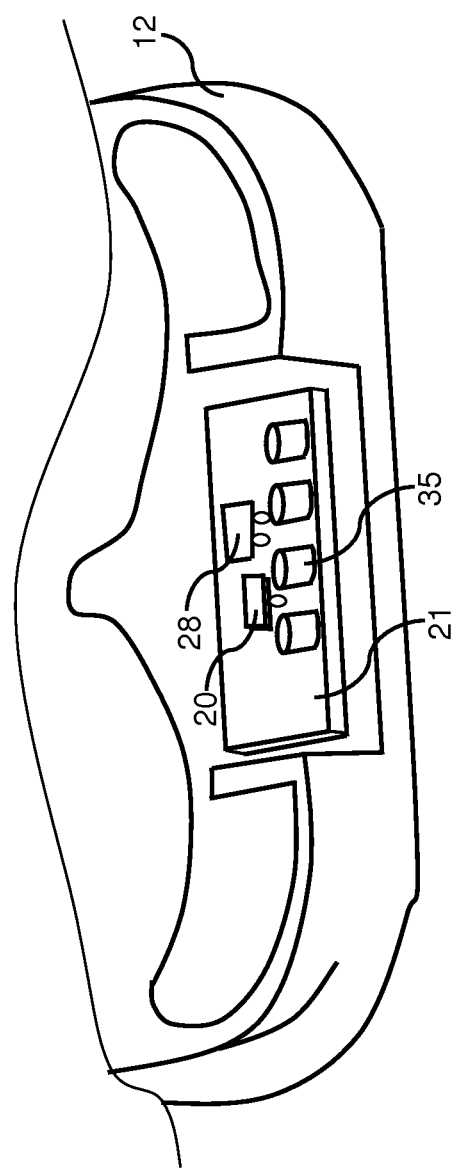
FIG. 6
(PriorArt)

SYSTEM, METHOD, AND APPARATUS FOR REFURBISHMENT OF ROBOTICALLY CONTROLLED DEVICES

FIELD

This invention relates to the field of electro-mechanical devices and more particularly to a system, method, and apparatus for extending the useful life of electro-mechanical devices such as robotic medical devices.

BACKGROUND

There are many electro-mechanical devices that include a subsystem that, after a prescribed number of uses, is no longer deemed reliable and, hence, is disabled. One example is where the electro-mechanical device is a robotic medical device connected to a control system. Over the past years, the field of surgery has progressed to a point in which many operations are performed robotically under the control of a surgeon who controls the operation of an arm that is maneuvered into the patient's body, perhaps through a small incision. Many procedures are now routinely performed using various robotically-enabled procedures. Procedures that previously required many days of hospital rest, such as removal of a gallbladder, now are performed with a minimally invasive incision without a hospital stay.

In such procedures, one or more robotic devices are interfaced, both physically and electrically to a control system that is operated by the surgeon. The devices are remotely controlled operating tools such as monopolar cautery instruments, wrist bipolar cautery instruments, ultrasonic energy instruments, wrist clip appliers, wrist needle drivers, wrist graspers, wrist scissors, wrist scalpels, laser energy instruments, wrist needle drivers, etc. The control system typically emits electrical signals under direction of the surgeon and the electrical signals are received by the robotic devices, interpreted, and result in electro-mechanically generated movement of an instrument at an end of the robotic devices. The surgeon has vision of what is happening within the patient during such procedures, typically by way of a camera or X-ray device (often called a C-arm).

After the procedure is performed, the robotic devices must be cleaned and sterilized so as not to pass any biological agents from one patient to the next patient. Such cleaning often includes chemical treatment such as those performed with an oxidant like peroxide or sterilization using heat treatment as performed under high moisture and pressure in an autoclave.

Manufacturers of the robotic devices created ways to limit the use of each robotic device to a certain number of uses. For example, some robotic devices are only allowed to be used ten (10) times, at which time that robotic device is disabled and cannot be used again. Likewise, manufacturers of other electro-mechanical devices also artificially restrict the number of usage cycles for their electro-mechanical devices, either for reliability reasons or for financial reasons.

Artificial disablement of these complex electro-mechanical devices has many negative effects, the first of which is financial, in that, the user (e.g., hospital, surgery center, etc.) must pay for new devices when the maximum use count is reached. Many such electro-mechanical devices are often very expensive, the cost of which is eventually borne by the end recipient of the functionality, often the hospital patient. Another negative effect is ecological. Such electro-mechanical devices become waste after they are disabled, adding to the piles of disposable electro-mechanical products that already fill our landfills. Another negative effect is the possibility of spreading diseases such as Methicillin-resistant *Staphylococcus aureus* (MRSA), etc. Being that the spent electro-mechanical device is of no further use to the organization (e.g., the hospital), after the final use, it is possible that the organization does not perform the final sterilization cycle and the device, hopefully, becomes biohazard waste, and hopefully is disposed according to biohazard disposal procedures, but there is always the risk or improper disposal and contamination.

Fortunately, with modern cleaning and refurbishment systems, the life of the robotic devices has increased, at least to a life greater than ten uses. With proper cleaning, maintenance, and periodic refurbishment of parts that may wear, it is possible to use many of these electro-mechanical devices or robotic devices for significantly more cycles than previously thought possible. This withstanding, manufacturers of these electro-mechanical devices or robotic devices continue to artificially limit the number of cycles to a small number and do not typically provide for refurbishment of the devices. This leads organizations such as hospitals to purchasing many more of the electro-mechanical devices or robotic devices than are actually needed; resulting in higher costs to patients for many procedures typically performed using such robot devices.

Such robotic devices often cost thousands of dollars. Other costs include logistics in ordering, stocking, shipping, keeping track of how many uses remain, etc. Furthermore, because of the potential harboring of biological agents, premature disposal of the robotic devices results in increases in biological waste created by the medical institutions, often characterized as bio-hazard waste, increasing the cost of disposal.

With proper care and periodic maintenance, any robotic devices will function properly for hundreds of procedures. Even though it is possible to repair and/or refurbish a large class of robotic devices, the artificial mechanisms created to limit the number of uses of such robotic devices often impede the refurbishment and reuse of such robotic devices after a pre-determined number of uses.

What is needed is a system, method, and apparatus for bypassing artificial mechanisms designed to limit the number of uses of robotically controlled devices and, therefore, enabling refurbishing of these robotically controlled devices to reduce costs and reduce impact on the environment.

SUMMARY

In a system in which a first device (e.g., a control system) affects operation of a plurality of removable devices (e.g., a robotic arms or the like), there is often a protocol and handshake between the first device and the removable devices, when attached, that provides information to the first device. Depending upon the protocol and handshake, the first device discovers certain properties of the removable device when it is attached to the first device (e.g., electrically and physically attached) such that the first device will understand the capabilities and, perhaps, the history of the now attached device. In many such systems, usage of the attached device is discovered and updated by the first device and, in some such systems, when a certain usage is achieved, the attached device is disabled by setting values within the attached device through the protocol and handshake that, when another attempt is made to use the attached device, the first device does not permit use.

Some removable devices have a simple memory device that contains identification information (e.g., serial numbers)

and usage data. In such, each time the removable device is used, the first system decrements usage counts. When the usage counts reach a predetermined value, the next time the removable device is attached to the first device, the first device indicates that the removable device is no longer usable and should be discarded. In this mode of operation, during refurbishment of the removable device, an interceptor device inserted between the first system and the removable device, preferably associated with and/or installed within the removable device. The interceptor device provides a programmed, refurbished usage count to the first system that then believes there are more uses remaining. This solution extends the useful life of the removable device, but does not provide any control over the number of uses and the removable device may eventually fail and potentially cause bodily injury. To reduce such possibilities, the interceptor is programmed with a programmable usage count and responds to the protocol and handshake as did the removable device, decrementing the programmable usage count until the number of programmed usages expires, at which time the removable device must be again refurbished and at which time the programmable usage count is reset.

In some systems, the first system reads certain information that is required before the attached system is used (e.g., serial number and usage counts). As above, the usage count is mimicked, but the first system will not properly proceed without the certain information, so the request for the certain information is forwarded to the attached device and the response from the first device is passed back to the first system by the interceptor.

In some systems, after detecting an expired attached device, the first system attempts to permanently disable the attached system by, for example, overwriting key data in the attached system that is needed for operation (e.g., serial numbers, identification). Unfortunately, due to the operation of certain attached devices, once the key data is overwritten, there is no way to correct the key data. There are several solutions to overcome this situation. One simple solution is to refurbish the attached system and install the interceptor before expiration, so the first system never detects the initial expiration and does not have an opportunity to overwrite the key data. In such, it is still desired to control the number of uses before the next refurbishment, so the interceptor has a usage counter, but when the interceptor's usage count expires and the first system attempts overwrites of the key data, the interceptor blocks the overwrite operation. In some solutions, the removable device has a memory that, prior to installation of the interceptor, is overwritten directly by the first device through the protocol and handshake, which typically includes a required programming voltage (e.g. 12V instead of 5V or 3.3V) or an independent program pin. In the former, a voltage limiting device or diode (e.g. ESD diode or Zener diode) is bridged over the interface to this memory device and the knee voltage of the voltage limiting diode is selected to pass anticipated interface signaling voltages (e.g. 3.3V or 5V) but block the programming voltage. For example, a 4V voltage limiting diode allows the 0-3.3V signals to pass but blocks the 12V programming signal. In the latter, the independent program pin is isolated (e.g., cut and biased to 'zero' or 'one' as needed), preventing programming requests to reach the memory. These will work for some systems, as long as the first device does not require a read-back of the overwritten data, which will not match since the data is not actually being overwritten. In that case, the interceptor needs to be inserted in the interface before the terminal count is reached so that when the first system attempts to overwrite the key data, the interceptor will prevent the overwrites from reaching the memory and will respond to the first system in a way that is expected by the first system.

In one embodiment, a device for extending the life of a robotically controlled device is disclosed. The robotically controlled device has an electrical interface for communicating between a control system and a robotically controlled device-based circuit mounted within the robotically controlled device. The device for extending the life of the robotically controlled has a circuit that is connected to the electrical interface. The circuit has a logic array that intercepts requests from the electrical interface such that the logic array recognizes at least one request from the control system and the logic array responds to the at least one request by sending a response to the control system over the electrical interface. At least one other request is forwarded by the logic array to the robotically controlled device-based circuit of which a response from the robotically controlled device-based circuit is received by the logic array and the response is forwarded by the logic array to the control system over the electrical interface.

In another embodiment, a method of refurbishing a robotically controlled device is disclosed. The robotically controlled device has an interface for communicating between a control system and a robotically controlled device-based circuit for storing data associated with the robotically controlled device. The robotically controlled device-based circuit is physically interfaced to the robotically controlled device and is electrically connected to the control system through one or more conductors. The method of refurbishment includes isolating at least one of the conductors into two sets of conductors, a first set of conductors of the two sets of conductors for communicating with the control system and a second set of conductors of the two sets of conductors for communicating with the robotically controlled device-based circuit. A circuit is inserted between the first set of conductors and the second set of conductors. The circuit has a first interface connected to the first set of conductors and a second interface connected to the second set of conductors. The circuit recognizes at least one request from the first interface and the circuit responds directly to the at least one requests. Likewise, the circuit forwards at least one other request from the first interface to the second interface and the circuit forwards a response from second interface back to the first interface.

In another embodiment, a device for extending the life of a robotically controlled device is disclosed. The robotically controlled device has electrical interface for communicating between a control system and a robotically controlled device-based circuit mounted within the robotically controlled device. The device for extending the life of the robotically controlled device includes a circuit that is connected to the electrical interface. The circuit has a logic array that intercepts requests from the electrical interface such that the logic array recognizes at least one request from the control system and the logic array responds to the at least one request by sending a response to the control system over the electrical interface and such that at least one other request is forwarded by the logic array to the robotically controlled device-based circuit of which a response from the robotically controlled device-based circuit is received by the logic array and the response is forwarded by the logic array to the control system over the electrical interface.

BRIEF DESCRIPTION OF THE DRAWINGS

The invention can be best understood by those having ordinary skill in the art by reference to the following detailed description when considered in conjunction with the accompanying drawings in which:

FIG. 6 illustrates a pictorial view of an exemplary electrical circuit board arrangement of an exemplary robotic device of the prior art.

DETAILED DESCRIPTION

Figure 1:
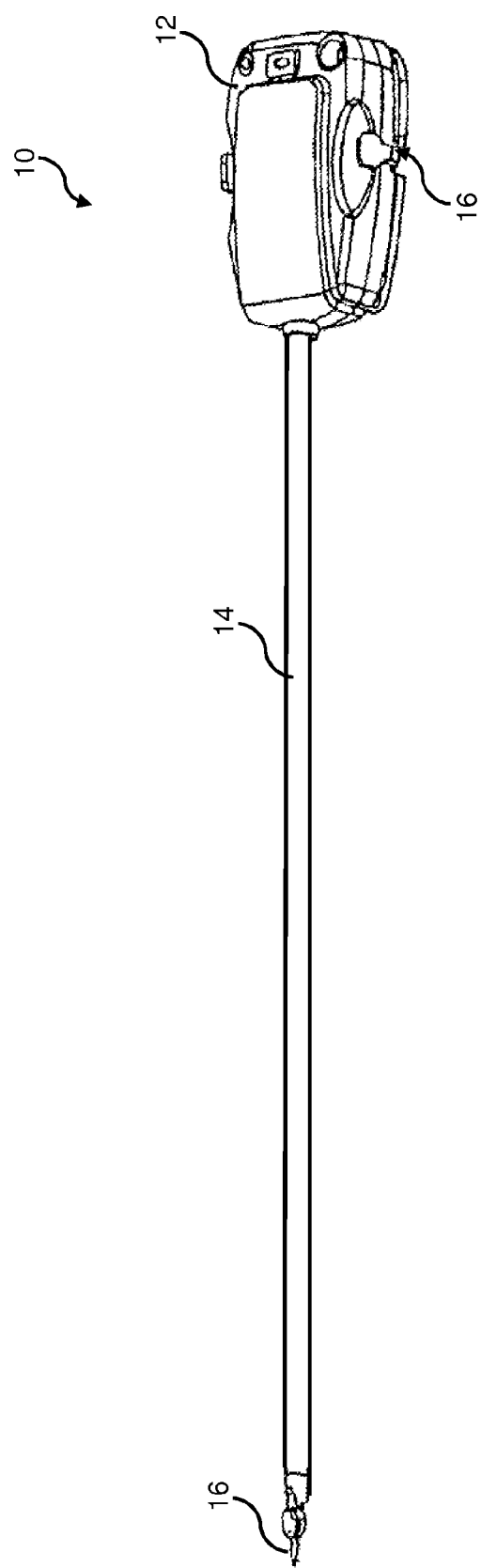
FIG. 1 illustrates a pictorial view of an exemplary robotic device of the prior art.

Reference will now be made in detail to the presently preferred embodiments of the invention, examples of which are illustrated in the accompanying drawings. Throughout the following detailed description, the same reference numerals refer to the same elements in all figures.

Throughout this document, the description uses a particular type of robotic surgical system as an example of many remote control systems. Such remote control systems have a common set of core features including a robotic control system and one or more robotic devices that selectively and removably interface to the robotic control system. Another common feature of such systems is that, for any of a multitude of reasons, the robotic control system has a way to determine the identification of the robotic device and, in some embodiments, to determine a history of the robotic device such as the number of uses, hours of usage, etc.

Throughout this document, the remote control systems are described as having a robotic control system 70 (see FIG. 2) that accepts inputs (e.g., from a user, surgeon, etc.) and causes one or more robotic devices 10 (see FIG. 1) to perform a related task based upon the inputs. Any robotic devices 10 are anticipate, for example, robotic arms. The robotic device 10 is typically installed/connected to a robotic control system 70 then used to perform certain tasks (e.g., cutting tissue, cauterizing, stapling), and then the robotic device is removed/disconnected from the control system 70.

In use, a robotic device 10 that is configured to cut tissue is connected to a robotic control system 70. Now, if user input requires that this robotic device 10 is to perform the cut operation, the robotic control system 70 signals the robotic device 10 to operate and cut. In some remote control systems, the robotic control system 70 is mechanically interfaced to the robotic device 10 by mechanical linkages and an electromechanical device such as a servo motor, actuator, etc., within the robotic control system 70 is energized and effects movement of the mechanical linkage to cause the robotic device 10 to perform the task (e.g., cut, cauterize). In some systems, the robotic control system 70 is electrically interfaced to the robotic device 10 by, for example, a communications link, and an electromechanical device such as a servo motor, actuator, etc., within the robotic device 10 is energized and effects movement of the mechanical linkage to cause the robotic device 10 to perform the task (e.g., cut, cauterize).

In some systems, the controlled robotic device 10 is primarily mechanical, in that, mechanical linkages between the removable robotic device 10 and the robotic control system 70 effect movements of components of the robotic device 10 and, therefore, there is little functional need for an electrical interface between the removable robotic device 10 and the robotic control system 70. In many such systems, designers have added an electrical interface and a device associated with the robotic device 10 that communicates with the robotic control system 70 through the electrical interfaces. In some such systems, the device associated with the robotic device is passive, in that, it acts as a memory that the robotic control system 70 reads and writes. In other such systems, the device associated with the robotic device 10 is active, having logic or processing capability.

In some systems, the controlled robotic device 10 is electro-mechanically driven or partially electro-mechanically driven along with mechanical, in that, at least some of the operation of the removable robotic device 10 is operated by electro-mechanical devices associated with the robotic device 10 and the robotic control system 70 effects movement of components of the robotic device 10 driven by the electro-mechanical drivers through an electrical interface between the removable robotic device 10 and the robotic control system 70. In such systems, there is sometimes present an electrical interface through which a circuit associated with the robotic device 10 communicates with the robotic control system 70 through. In some such systems, the device associated with the robotic device 10 is passive, in that, it acts as a memory that the robotic control system 70 reads and writes. In other such systems, the device associated with the robotic device 10 is active, having logic or processing capability.

There exist systems having robotic control systems 70 and multitudes of controlled, removable robotic devices 10 in which each removable robotic device 10 has integrated memory 28 (see FIG. 2) that is used by the robotic control system 70 for various reasons. Such memory 28 is often used to store identification information that indicates the type and serial number of the robotic device 10 to the robotic control system 70. This is useful in configuring the robotic control system 70 to properly operate the robotic device 10 and to assure that a proper robotic device 10 is present. Another use for such memory is to track usage of each robotic device 10. Being that the robotic devices 10 are portable and it is anticipated that an organization will have several robotic control systems 70 and several removable robotic devices 10, usage data needs to be associated with each robotic device 10, and therefore, the best place to keep such data is in the integrated memory 28. When the robotic device 10 is connected to a particular robotic control system 70, the robotic control system 70 reads the usage data and determines if the robotic device 10 has had too many uses. In many systems, once the usage reaches a certain level (such as ten uses or eight hours of operation), the robotic device 10 is disabled by the robotic control system 70 and will no longer operate. In many such systems, once a usage is subtracted from the integrated memory 28, there is no way to go back and change that value, even if the robotic device 10 is later refurbished (e.g., cleaned, inspected, lubricated, worn parts replaced).

In some systems, after the usage data reaches the terminal count, the robotic control system 70 overwrites key data required for operation of the robotic device 10, further de-capacitating the robotic device 10. In such, steps are taken to prevent this overwrite such as installing the disclosed interceptor before the terminal count is reached (e.g. after 9 uses in a device that is allowed 10 uses) or by preventing the overwriting.

Although the following description shows one particular medical implementation of a robotic control of one or more removable robotic devices 10, the present invention is not limited to the medical field and applies to any system in which multiple removable robotic devices 10 are, at times, installed onto a robotic control system 70 and controlled by the robotic control system 70 to perform functions.

Referring to FIG. 1, a pictorial view of an exemplary removable robotic device 10 of the prior art is shown. Note that for brevity reasons, the removable robotic device 10 will often be referred to as the robotic device 10 and this refers to the device 10 that performs a function as controlled by the robotic control system 70. For many removable robotic devices 10, there are several interfaces between the robotic control system 70 and the robotic device 10, including any of mechanical interfaces, electrical interfaces, magnetic interfaces, wireless interfaces, etc. The following description will focus on the electrical interface as the mechanical interface is well known in the industry and not changed by the present invention.

In such exemplary removable robotic devices 10, a control interface 12 attaches to a control system 70 through, for example, mechanical linkages (not visible) and an electrical interface 16. An elongated shaft 14 transfers movements from the mechanical linkages to control and move an active device 16 at the end of the elongated shaft 14, such as movement of a scalpel, etc. As discussed, the linkages are typically mechanical having, for example, servo motors or actuators associated with the control system 70 that are mechanically linked to the control interface 12, although in some exemplary removable robotic devices 10, the servo motors, actuators, etc., are housed within the control interface 12 and are controlled by electrical signals through the electrical interface 16.

In some exemplary removable robotic devices 10, the electrical interface 16 is solely present only for identification and status purposes, such as to communicate to the control system which exemplary removable robotic device 10 out of a set of exemplary removable robotic devices 10 is attached to the control system.

Often, a storage device 28 (see FIG. 2) within the control interface 12 includes counters that keep track of the usage of the exemplary removable robotic device 10. Such counters often track usage data such as number of uses or cumulative usage time. Manufactures of some removable robotic device 10 often program the control systems 70 to read this usage data to determine when the exemplary removable robotic device 10 should no longer be used. For example, after using certain exemplary removable robotic devices 10 ten times, the control system disables the use of that exemplary removable robotic device 10. This robotic device 10 is henceforth inoperable. Even after proper cleaning, inspection, and replacement of components that have wear, these "use counters" continue to prevent the use of such exemplary removable robotic devices 10. In some control systems 70, after determining that the robotic device 10 has no more uses available, the control system 70 overwrites key or random areas of the memory 28, further impacting refurbishment.

There are many ways known to communicate and update usage data between the control system 70 and the exemplary removable robotic devices 10. Most utilize an electrical interface 16 to convey electrical signals between the control system and a device within the control interface 12, though any interface 16 is anticipated including wireless interfaces such as near-field/Bluetooth, magnetic interfaces, optical interfaces, etc. In one example, a device within the control interface 12 is a standard memory device 28 having a single wire electrical and logic interface (plus ground) that is well defined both electrically and by a fixed protocol, such that, the control system 70 reads and writes data to/from this memory device 28 through the 22 interface as defined by the manufacturer of the memory device 28. Such memory devices 28 often have a unique serial number that can be read by the control system 70 to uniquely identify the removable robotic device 10. In some control systems 70, this unique serial number is used to identify the robotic device 10, while some other control systems 70, a serial number is stored elsewhere in the memory device 28 and this serial number is used to identify the robotic device 10.

In this simple, single wire interface 22 (see FIG. 2), it is possible to write to the memory device 28. Therefore, the control system 70 will read the number of previous uses to make sure the robotic device 10 hasn't expired, and then after another use is complete, the control system 70 will write an updated number of uses that includes the current use. Often such memory devices 28 permit the changing of a memory value from zero to one or from one to zero only, and not vice versa. Therefore, these memory devices 28 work very well for preventing usage past a certain predetermined usage allowance. As an example, when new, the memory 28 within the exemplary removable robotic device 10 has a set of ten bit registers, each having an initial value of one. Each time the removable robotic device 10 is used, a successive one of the bit registers is set to zero (through a transaction from the robotic control system 70). After the last bit register is set to zero (all bit registers are now zero), upon initialization, the control system 70 reads the bit registers and, being that all are zero, the control system 70 prevents usage of the removable robotic device 10. Since the bit registers cannot be rewritten to a value of one, there is no way to change the bit register values to a value of one to allow additional uses.

Figure 2:
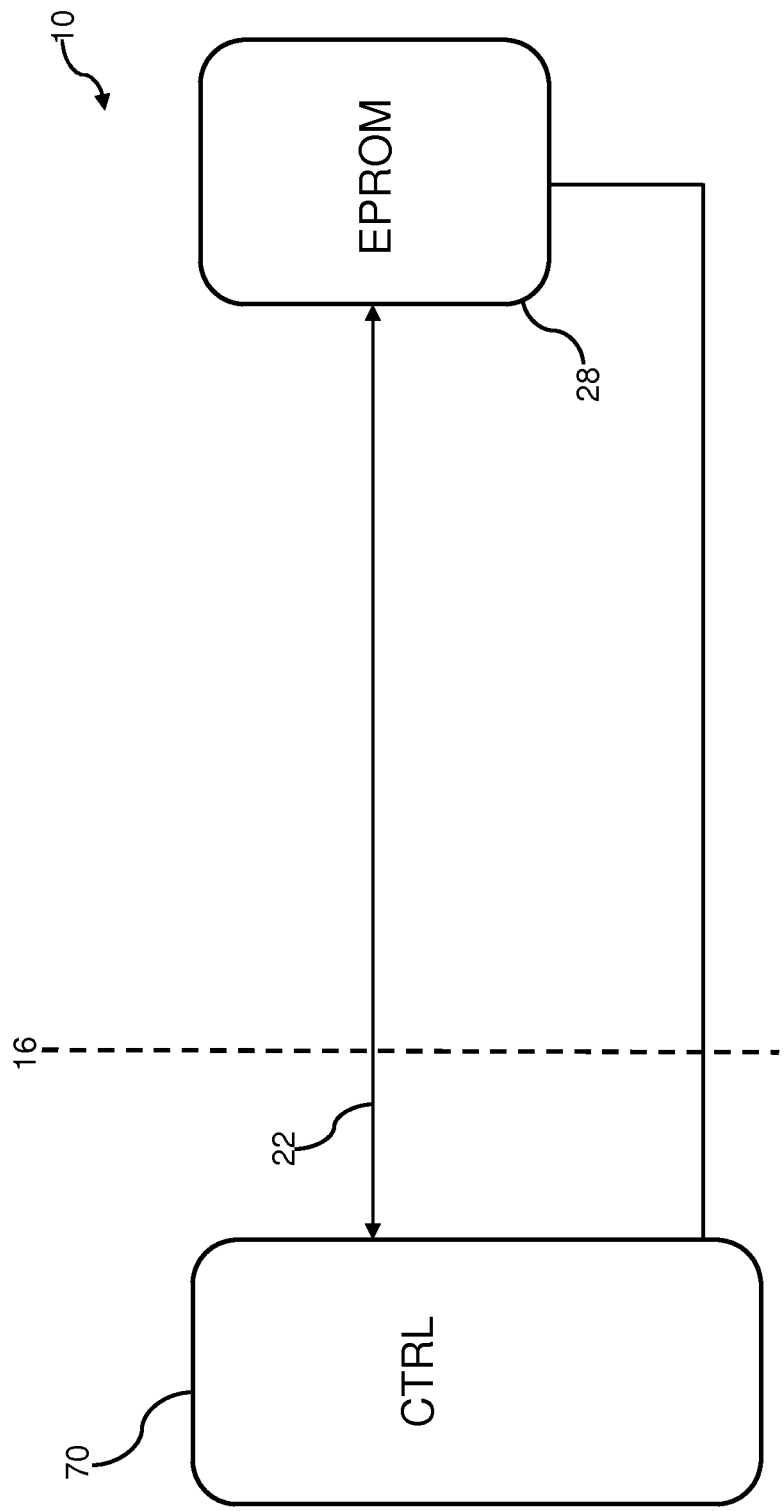
FIG. 2 illustrates a schematic view of an exemplary electrical arrangement between an exemplary robotic control system and an exemplary robotic device of the prior art.

Referring to FIG. 2, a schematic view of an exemplary electrical arrangement between an exemplary robotic control system 70 of the prior art and an exemplary robotic device 10 of the prior art is shown. This exemplary interface uses a single wire interface 22 to communicate between the control system 70 and the integrated memory device 28. Therefore, the control system 70 reads the number of previous uses from the robotic memory device 28 before enabling use of the robotic device 10, and then after, for example, another use is complete, the control system 70 writes an updated number of uses that includes the current use. One such exemplary memory 28 permits the changing of a memory value from zero to one or from one to zero only, and not vice versa. As an example, when new, the exemplary robotic device 10 has a set of ten bit registers within the robotic memory device 28, each having an initial value of one. Each time the removable robotic device 10 is used, the control system 70 reads the ten bit registers to make sure that at least one of the ten bit registers contains a one value, and then a successive one of the bit registers is written to a zero value. After the last bit register is set to zero (all bit registers are now zero), when the control system 70 reads the bit registers, the control system 70 prevents usage of the removable robotic device 10 being that all bit registers are zero. Since the bit registers cannot be rewritten to a value of one, there is no way to change the memory values to allow additional uses of the robotic device 10.

In this exemplary robotic device 10, the robotic memory device 28 receives control protocol commands from the single wire interface 22 (e.g., read location, write location), performs the desired operation on the robotic memory device 28 (e.g., EPROM), and reports back results through the protocol over the single wire interface 22, such as the contents of the read location or acknowledgement of the write operation succeeded. Although in many implementations the robotic memory device 28 is powered by the single wire interface 22, e.g., through internal power conditioners or diodes, it is equally anticipated that in some embodiments supplemental power is provided (e.g., by a battery, wireless power source, external power source) or through additional connections of the interface 16.

Note that, although the descriptions provided use an exemplary single wire interface 22, there is no limitation on any specific configuration of interface 16 and any known or future interface is anticipated, serial or parallel, utilizing any protocol.

Figure 3:
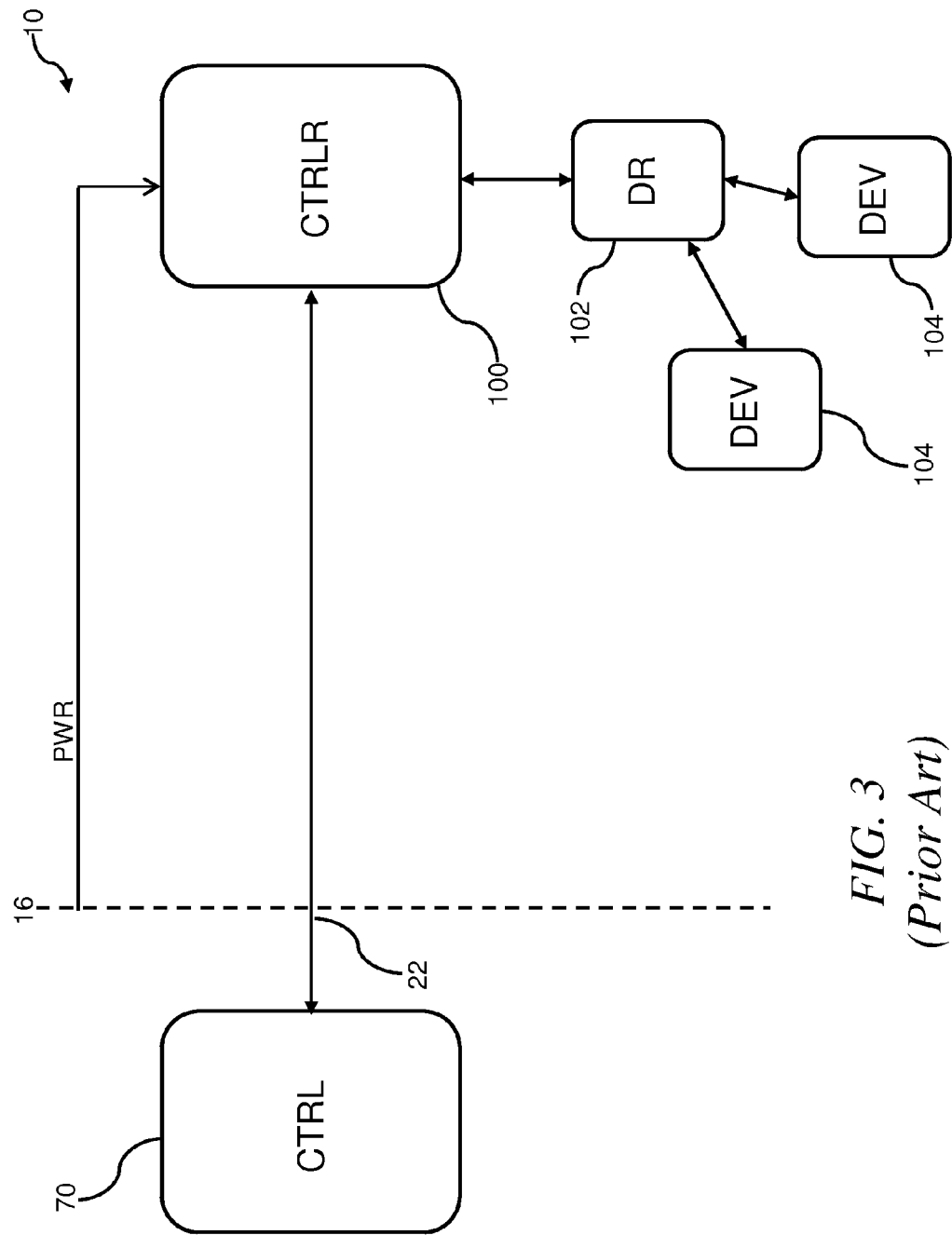
FIG. 3 illustrates a schematic view of a second exemplary electrical arrangement between an exemplary robotic control system of the prior art and an exemplary robotic device of the prior art.

Referring to FIG. 3, a schematic view of a second exemplary electrical arrangement between an exemplary robotic control system 70 of the prior art and an exemplary robotic device 10 of the prior art is shown. This second exemplary arrangement utilizes an active device 100 (e.g., processor or logic array) within the robotic device 10. In such, in addition to tracking usage counts, serial numbers, and other data, the active device 100 (in some embodiments) also controls operation of one or more electromechanical devices 104 through, for example, driver electronics 102. In such, in addition to the protocols for reading/writing usage counts sent through the interface 16, operation commands are also sent through the interface 16 (e.g., single wire interface 22) to operate the electromechanical devices 104 (e.g., servos, actuators).

Figure 4:
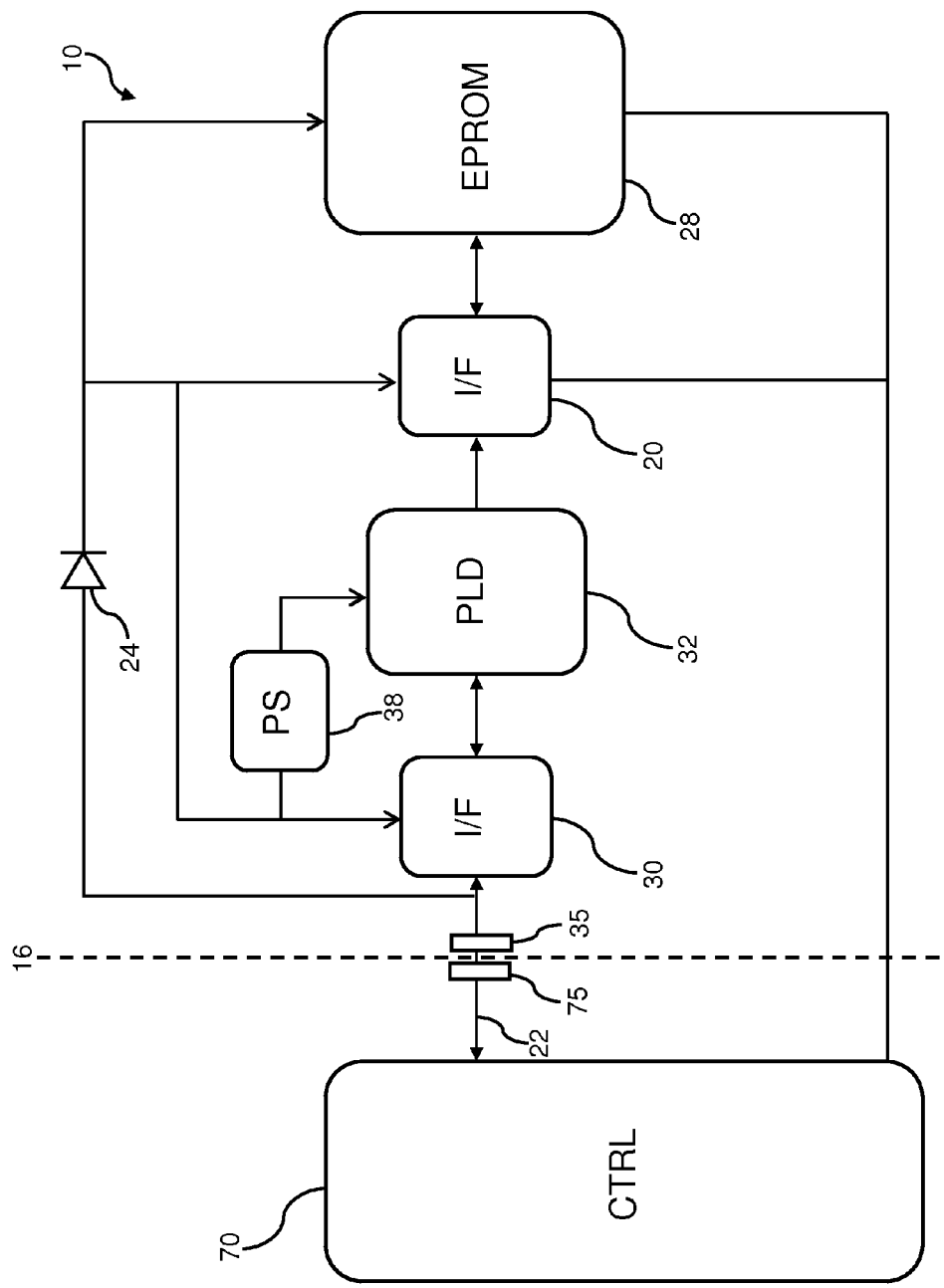
FIGS. 4 and 4A illustrate schematic views of exemplary electrical arrangements between an exemplary robotic control system of the prior art and an exemplary robotic device modified with an interceptor system.
Figure 4A:
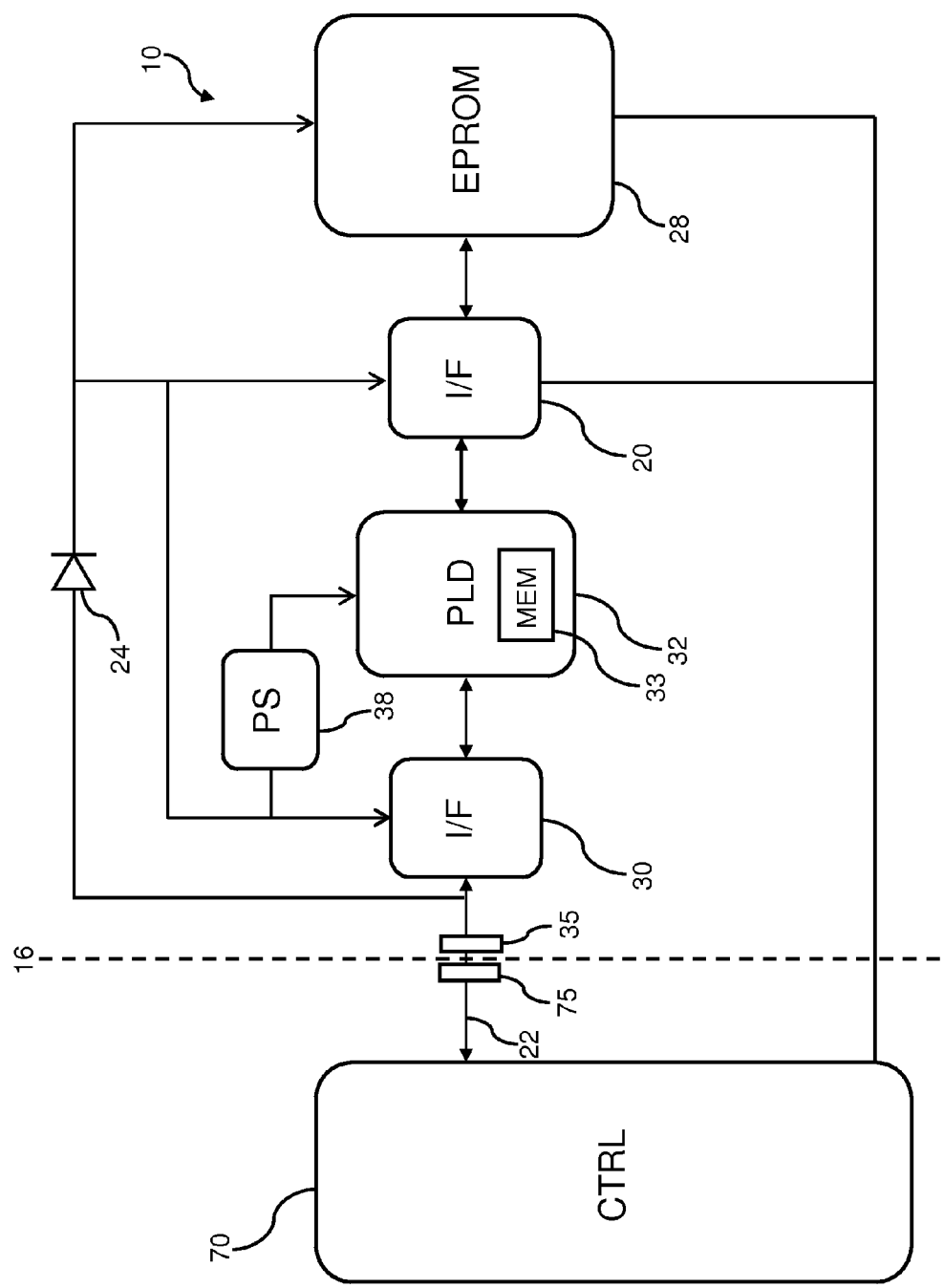

Referring to FIGS. 4 and 4A, schematic views of an exemplary electrical arrangement between an exemplary robotic control system 70 and an exemplary robotic device 10 modified with an interceptor system is 32 shown. As described previously, the exemplary interface 16 uses a single wire interface 22 to communicate between the control system 70 and exemplary robotic device 10. In this exemplary modified robotic device 10, an interceptor 32 is inserted between the robotic control system 70 and the memory device 28, although in alternate embodiments, the interceptor 32 is bridged onto the connection between the control system and the memory device 28. The memory device 28, therefore, receives control protocol commands from the logic array 32 instead of from the control system 70. The robotic memory device 28 (e.g., EPROM) receives commands and data from the logic array 32 and reports back results to the logic array 32 through the same protocol over the single wire interface 22. The control system 70 believes that it is communicating directly with the memory device 28 through the single wire interface 22, but instead, the robotic control system 70 is communicating with the interceptor 32. In the exemplary embodiment shown, optional interface devices 20/30 are present to provide clean logic signals to the control system 70, interceptor 32, and/or the robotic memory device 28.

The interceptor 32 receives and responds to commands from the robotic control system 70 and, in a preferred embodiment, is a logic array 32 for making decisions regarding commands sent from the control system 70. For example, most commands for reading the robotic memory device 28 are received by the logic array 32 and processed by forwarding the exact command to the existing robotic memory device 28. When the robotic memory device 28 returns data or status, for some transactions, the data or status is passed back through the interceptor 32 to the control system 70. For other transactions, a programmed response is instead passed back emanating from the interceptor 32 and the original response from the robotic memory device 28 is ignored.

In embodiments in which the interceptor 32 is bridged onto the connection between the control system and the memory device 28, the interceptor 32 receives and responds to commands from the robotic control system 70 and the logic array 32 selectively sends reset signals to the memory device 28 to prevent writing of data to the memory 28. For example, most commands for reading the robotic memory device 28 are received by the intercept 32 at the same time they are received by the existing robotic memory device 28. When the interceptor 32 recognizes, for example, a write command from the control system 70, in this embodiment, that write command has already been received by the robotic memory device 28 and the robotic memory device 28 is expecting address and/or data next. To preclude writing to the robotic memory device 28, a reset signal is emitted by the interceptor 32 that resets the robotic memory device 28, thereby canceling the write operation.

For certain transactions, the interceptor 32 programs responses to provide some data or prevents the writing of some data to enable usage of the robotic device 10 beyond the number of uses originally and permanently set by the manufacturer. In some embodiments, the interceptor 32 suppresses writing to the usage registers, while in other embodiments, the interceptor 32 has an internal usage counter 33 (see FIGS. 4A and 5A) that is used to generate a response that the interceptor sends to the control system 70. In some embodiments, the number of remaining uses in the internal usage counter 33 is resettable during refurbishment. In some embodiments, when the control system 70 attempts to write to the usage counter (e.g., changing seven uses to eight uses by clearing a bit register via a write operation), the operation is bypassed by the interceptor 32. In other embodiments, the interceptor 32 issues programmed responses to the control system indicating that there are more uses remaining than originally set by the manufacturer by issuing programmed responses containing a usage count that is different than what is stored in the memory device 28. For example, in some embodiments as shown in FIG. 4, when the control system 70 requests (reads) the number of previous uses, that request is passed through the logic array 32 to the interface 20 and the number of remaining uses is read from the robotic memory device 28 and relayed back to the logic array 32. If the number of remaining uses is zero, the logic array 32 encodes a value in the response to indicate that more uses remains and relays the response back to the control system 70, issuing programmed responses to the control system 70 indicating that the robotic device 10 has remaining uses. If the number of remaining uses is at least one, the response containing that value is relayed to the control system 70. Alternately, the interceptor 32 simply issues a programmed response as the number of remaining uses, such as always responding with three uses remaining, etc.

In some embodiments, as shown in FIG. 4A, the interceptor 32 (e.g., logic array 32) has memory 33, preferably non-volatile memory such as flash memory, battery-backed up RAM, etc. In this embodiment, after refurbishment is performed on the robotic device 10, the interceptor memory 33 is programmed to indicate a pre-determined number of uses (e.g., ten uses). Note that, although it is anticipated that the number of uses is represented in the same or similar way as represented within the robotic memory device 28, there is no requirement of such. For example, it is anticipated that in some embodiments, the usage count is represented as four binary bits and the bits representing $2^3$, $2^2$, $2^1$, and $2^0$ as is often used in computer programming such that ten remaining uses is represented as 1010 and five remaining uses is represented as 0101, etc. Independent of how the usage count is represented in the interceptor memory 33, when the control system 70 requests (reads) the number of previous uses, that request is intercepted by the interceptor 32 and never reaches the robotic memory device 28. The number of remaining uses from the memory 33 is then sent back to the control system 70 in the format expected by the control system 70. It is further anticipated that, upon installation of the interceptor 32, the usage count in the interceptor memory 33 is set to an initial value that will limit the total number of usages, even with refurbishment. For example, the usage count is set to 50, enabling 50 total uses, but no more. Then, the number of remaining uses are reported as, for example, a mask or modulus of the total usages (e.g., mod 10) so if the count is 49, 9 is reported to the control system 70, etc. Then, when the count reaches 40, zero is reported to the control system 70 and the robotic device 10 is no longer usable until refurbishment, which includes decrementing of the usage count in the interceptor memory 33, for example to 39, until the usage count in the interceptor memory 33 reaches zero in which the robotic device 10 is no longer refurbishable.

After the present usage is complete, in some systems, the control system 70 sends a request to the robotic device 10 to write an updated number of uses that accounts for the current use. The interceptor 32 deciphers this request and either prevents transmission of the request to the robotic memory device 28 or passes the request, assuming at least one usage remains. Therefore, the usage count in the robotic memory device 28 is not updated or never reaches zero. In the embodiment of FIG. 4, the interceptor 32 prepares a programmed response to send to the control system 70 mimicking that the updated usage count has been properly written to the robotic memory device 28. In embodiments in which the interceptor 32 communicates to the control system 70 by, for example, returning a programmed number of remaining uses, it is likely that the number of uses sent from the interceptor 32 to the control system 70 is different than the number stored in the robotic memory device 28, and therefore, an attempt to write a usage count that is one less than the number that the interceptor 32 created will fail if passed on to the robotic memory device 28. Therefore, in this scenario, there is no attempt to write to the robotic memory device 28 and the command is recorded and programs a response with a value that the control program 70 would expect if the robotic memory device 28 was successfully written. In the embodiment of FIG. 4A, the interceptor 32 decrements the counter in the interceptor memory 33 and prepares a proper response to send to the control system 70. In this, the control system 70 is believes that the updated usage count has been properly written to the robotic memory device 28, where instead, the updated usage count is updated in the interceptor memory 33. In systems in which the control system 70 reacts to a "zero remaining use situation" by randomly or systematically overwriting key locations of the robotic memory device 28, in some embodiments, the interceptor 32 does not permit the usage counter in the interceptor memory 33 to reach zero, the interceptor 32 does not respond with a zero value, or the interceptor 32 allows the zero value response, but then subsequently intercepts and blocks the overwriting operations.

It is anticipated that some existing control systems 70 will at times, test the memory of the robotic device 10 by attempting to write a usage value that is not possible. In many embodiments of the robotic memory device 28, the memory is writable, but each bit can only be changed from one to zero, not from zero to one. This is why the usage count is typically stored as an array of bits, each bit representing one remaining use is available, instead of a counter that is decremented until it reaches zero. Knowing this, it is possible for the control system 70 to attempt a write operation that will not change at least one bit because that bit is at a zero value. For example, assume the usage count (as stored in the robotic memory device 28) is represented by 10 bits, 1111111111 representing 10 remaining usages. Now, assume that usage bits are consumed from right to left, so after the first use, the bits will be 1111111110 and after the second use, the bits will be 1111111100, etc. If two uses have already been recorded (1111111100) and the controller tries to write the usage value of 1111111101 or the usage value of 1111111110, the interceptor 32 will have logic to prevent the stored value from reflecting the change from 8 uses available to nine uses available. Therefore, even though the use count stored in the logic array is capable of incrementing, the interceptor 32 determines that the use count value being written by the control system 70 would not have set bits in the robotic memory device 28 of the prior art (see FIG. 2) and the interceptor 32 will perform logic steps to act and respond as expected by the control system 70. In this example, the interceptor memory 33 indicates that eight uses remain (e.g., either bits 1111111100 or a counter 1000) and the control system 70 tries to write a value that indicates nine uses remain (e.g., 1111111110), then the interceptor memory 33 remains at the present value and a representation of that value (e.g., 1111111100) is returned as a response to the control system 70, which is a similar response as would have been made by the robotic memory device 28 of the prior art.

In the embodiment of FIG. 4A, once the usage count stored in the interceptor memory 33 reaches zero, the robotic device 10 must be again refurbished, in which one of the steps of refurbishment is to reset the usage count in the interceptor memory 33 (e.g., to ten).

Although any powering scheme is anticipated, in the example shown, the existing interface 20 and robotic memory device 28 is powered by the single wire interface 22 (e.g., through diode 24). In this example, the interceptor interfaces 20/30 and logic array 32 are also powered from parasitic power from the single wire interface 22 by, for example, an auxiliary power supply 38. Being that the single wire interface 22 has limited power available and some of this power is already being consumed to power the existing robotic memory device 28, in some embodiments a power supply 38 is needed to store power (e.g., a capacitor) and/or pump up the voltage to a value that will operate the interceptor interfaces 20/30 and logic array 32. Although this power scheme is desired for many reasons, including cost, it is also anticipated that in alternate embodiments, the interceptor 32 is powered or supplemented by a power source, internal or external to the robotic device 10 such as a battery, solar panel, super capacitor, etc., the likes of which is typically installed or replaced during refurbishment.

Figure 5:
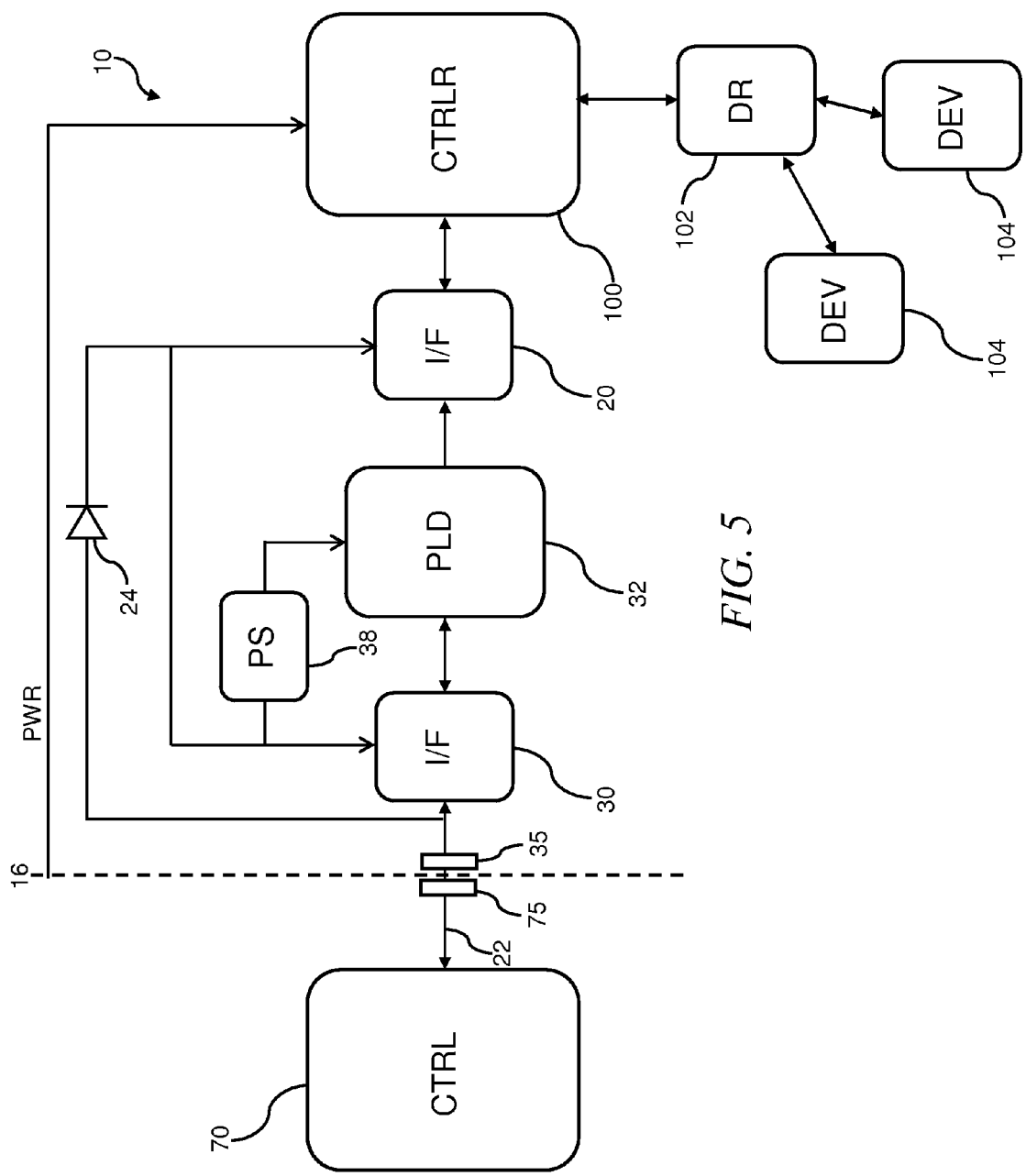
FIGS. 5 and 5A illustrate schematic views of second exemplary electrical arrangements between an exemplary robotic control system of the prior art and an exemplary robotic device modified with an interceptor system.
Figure 5A:
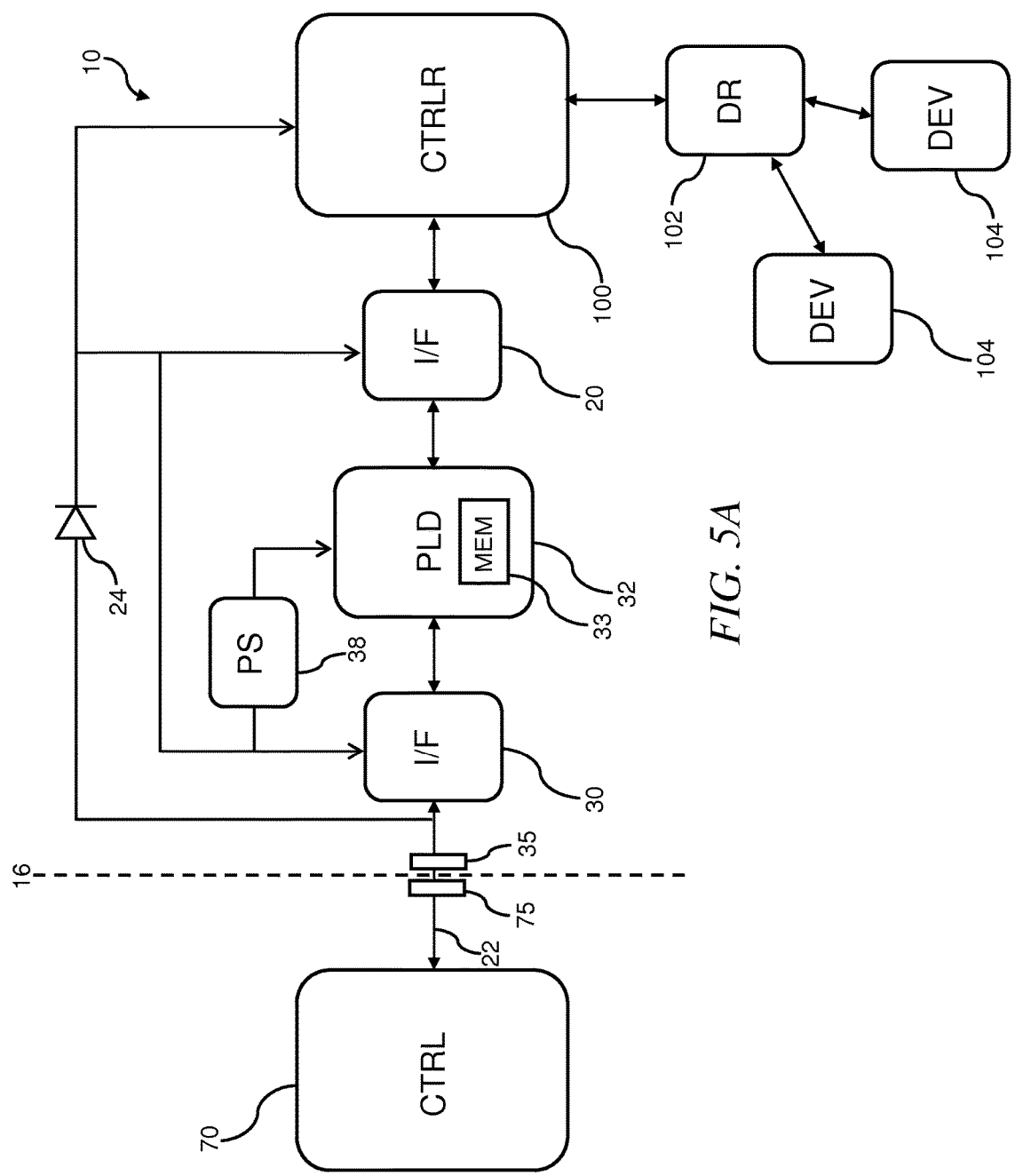

Referring to FIGS. 5 and 5A, schematic views of a second exemplary electrical arrangement between an exemplary robotic control system 70 and an exemplary robotic device 10 modified with an interceptor 32 is shown. In this embodiment, the interceptor 32 functions similar to the prior interceptor system 32 as described with FIGS. 4 and 4A, with the addition of processing additional device control commands that are sent from the robotic control system 70 to the embedded control device 100 of the robotic device 10. Therefore, the interceptor 32 must either forward all control commands from the robotic control system 70 through to the embedded control device 100 or the interceptor 32 must decode such commands and pass selected commands as needed while internally processing other commands such as commands dealing with usage counts. Likewise, the interceptor 32 passes response/status data from the embedded control device 100 to the robotic control system 70 from commands that are forwarded or the interceptor 32 creates programmed responses to, for example, requests dealing with usage counts, as needed.

Again, when usage data is requested by the robotic control system 70, the interceptor 32 intercepts this request and mimics or modifies the response sent back from the interceptor 32 to the robotic control system 70 to indicate that additional usage is available, above what is recorded in the robotic memory device 28. In the embodiment of FIG. 5, the interceptor 32 does not have persistent storage 33 (see FIG. 5A) and, therefore, does not count uses. Therefore, when the control system 70 requests usage data, the interceptor 32 only has the ability to respond with a pre-programmed count such as a fixed count (e.g., "1 use remaining"). Likewise, when the control system 70 requests a write operation to the usage data, the interceptor 32 suppresses that request from getting to the robotic memory device 28 and formulates a response that is sent to the control system 70 which believes that the operation succeeded.

Some control systems 70 have sufficient memory as to remember the uses remaining for some number of robotic devices 10. In this, if the control system 70 reads the uses remaining and the value returned does not match the expected uses remaining, the control system 70 does not allow use of that robotic device 10. To get around this issue, the embodiment of FIG. 5A includes an interceptor memory 33, preferably non-volatile memory such as flash memory, battery-backed up RAM, etc. In this embodiment, after refurbishment is performed on the robotic device 10, the interceptor memory 33 is programmed to indicate a pre-determined number of uses (e.g., ten uses). Note that, although it is anticipated that the number of uses is represented in the same or similar way as represented within the robotic device robotic memory device 28, there is no requirement or limitation of such. For example, it is anticipated that in some embodiments, the usage count is represented as four binary bits and the bits representing $2^3, 2^2, 2^1$, and $2^0$ as is often used in computer programming such that ten remaining uses is represented as 1010 and five remaining uses is represented as 0101, etc. Independent of how the usage count is represented in the interceptor memory 33, when the control system 70 requests (reads) the number of previous uses, that request is intercepted by the interceptor 32 and never reaches the interface 20. The number of remaining uses is then sent from the interceptor 32 to the control system 70 in the format expected by the control system 70.

After the present usage is complete, in some systems, the robotic control system 70 sends a request to the robotic device 10 to write an updated number of uses that accounts for the current use (decrements). The interceptor 32 deciphers this request and prevents transmission of the request to the robotic memory device 28 and the robotic memory device 28 is not updated. In the embodiment of FIG. 5A, the interceptor 32 decrements (or writes to) the counter in the interceptor memory 33 and prepares a proper response to send to the control system 70. In this, the control system 70 communication is provided a response that the updated usage count has been properly written to the robotic memory device 28, where instead, the updated usage count is now stored in the interceptor memory 33 instead. In this embodiment, once the usage count reaches zero, the robotic device 10 must be again refurbished in which, one of the steps of refurbishment is to reset the usage count within the interceptor memory 33 (e.g., to ten). Again, in some embodiments, the interceptor 32 mimics the existing robotic memory device 28, in that, if the existing robotic memory device 28 only allows changing of memory bits from 1 to 0, or only allows changing of memory bits from 0 to 1; the interceptor 32 understands the operation of the existing robotic memory device 28 and simulates the operation of the existing robotic memory device 28 by not permitting clearing of bits when the existing robotic memory device 28 would not allow clearing of bits or setting of bits when the existing robotic memory device 28 does not allow setting of bits.

In the embodiments shown in FIGS. 5 and 5A, a similar power scheme as in FIG. 4 is shown, though being that the robotic device 10 has active components, it is anticipated that ample power is available through the interface 16 for powering servos, actuators, etc., and, therefore, sufficient power is also available to power the interceptor 32.

Although the interceptor 32 is shown as with separate interceptor interfaces 20/30 and a logic array 32, in some embodiments both functions are combined into one device (not shown). Likewise, in some embodiments, the interceptor logic is embedded into a preferably low-powered, microcontroller or other computing device having an internal stored program for intercepting the usage commands and responding to the robotic control system 70 with modified usage indications.

Referring to FIG. 6, a pictorial view of an exemplary electrical circuit board arrangement of an exemplary robotic device 10 of the prior art is shown. The circuit board 21 includes the existing robotic memory device 28, along with interconnection paths, power devices, and any other components deemed necessary by the robotic device manufacturer (e.g., bypass capacitors, etc.). In the embodiment shown, the circuit board 21 also has several interface pins, such as the interface pin 35 that connects to a corresponding interface pin 75 (not shown) of the robotic control system 70 for communicating the single wire interface 22 between the robotic control system 70 and the robotic device 10. In this way, when the robotic device 10 is coupled to the robotic control system 70, the interface pins 35/75 make contact and conduct the single wire interface 22.

Figure 7:
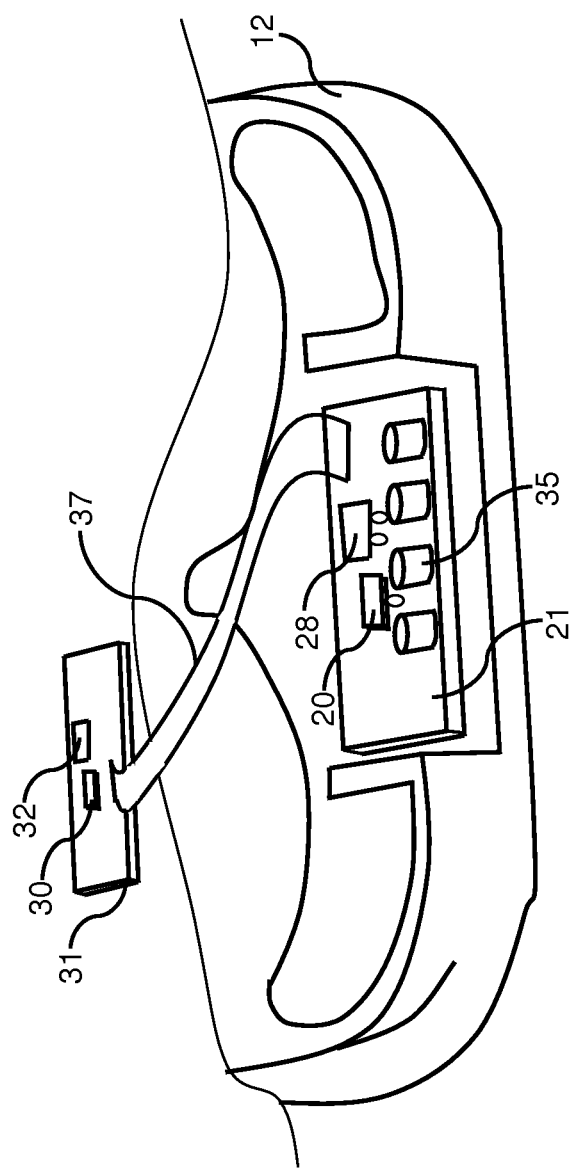
FIG. 7 illustrates a pictorial view of an exemplary electrical circuit board arrangement of an exemplary robotic device of the prior art modified with an electrical circuit board having an interceptor system.

Referring to FIG. 7, a pictorial view of an exemplary electrical circuit board arrangement of an exemplary robotic device 10 of the prior art modified with an interceptor electrical circuit board 31 having an interceptor 32 is shown. The electrical circuit board 31 is connected to the original circuit board 21 of the robotic device 10 through wires, ribbon cables, etc. 37. Paths or pins on the original circuit board 21 are intercepted and conductors of the wires, ribbon cables, etc. 37 attached to the interceptor circuit board 31 (e.g., by soldering). In some embodiments, the interceptor circuit board 31 is formed on a flexible circuit board 31 that also forms the connection path 37 to the original circuit board 21.

There are many ways to electrically interface the interceptor functionality to the original circuit board 21, and there are no limitations on such electrical and mechanical interface implied by the examples shown and provided. Additionally, because the robotic device 10 is often sterilized between uses, the original circuit board 21, the connecting conductors 37, and the interceptor electrical circuit board 31 are preferably (not required) encapsulated (e.g., potted) to prevent contact with cleaning agents used after each use.

In some embodiments, the interceptor 32 and optional interface devices 30/20 are mounted on the daughter circuit board 31 and pins are disconnected from the original circuit board 21 and connected through the cable 37. In some embodiments, the robotic memory device 28 is removed from the original circuit board 21 and installed on the daughter circuit board 31. In some embodiments, the original circuit board 21 is replaced with a modified circuit board 31 and the robotic memory device is removed from the original circuit board 21 and installed upon the modified circuit board 31. Any known way for inserting the interceptor 32 into the circuit is equally anticipated and included here within.

Figure 8:
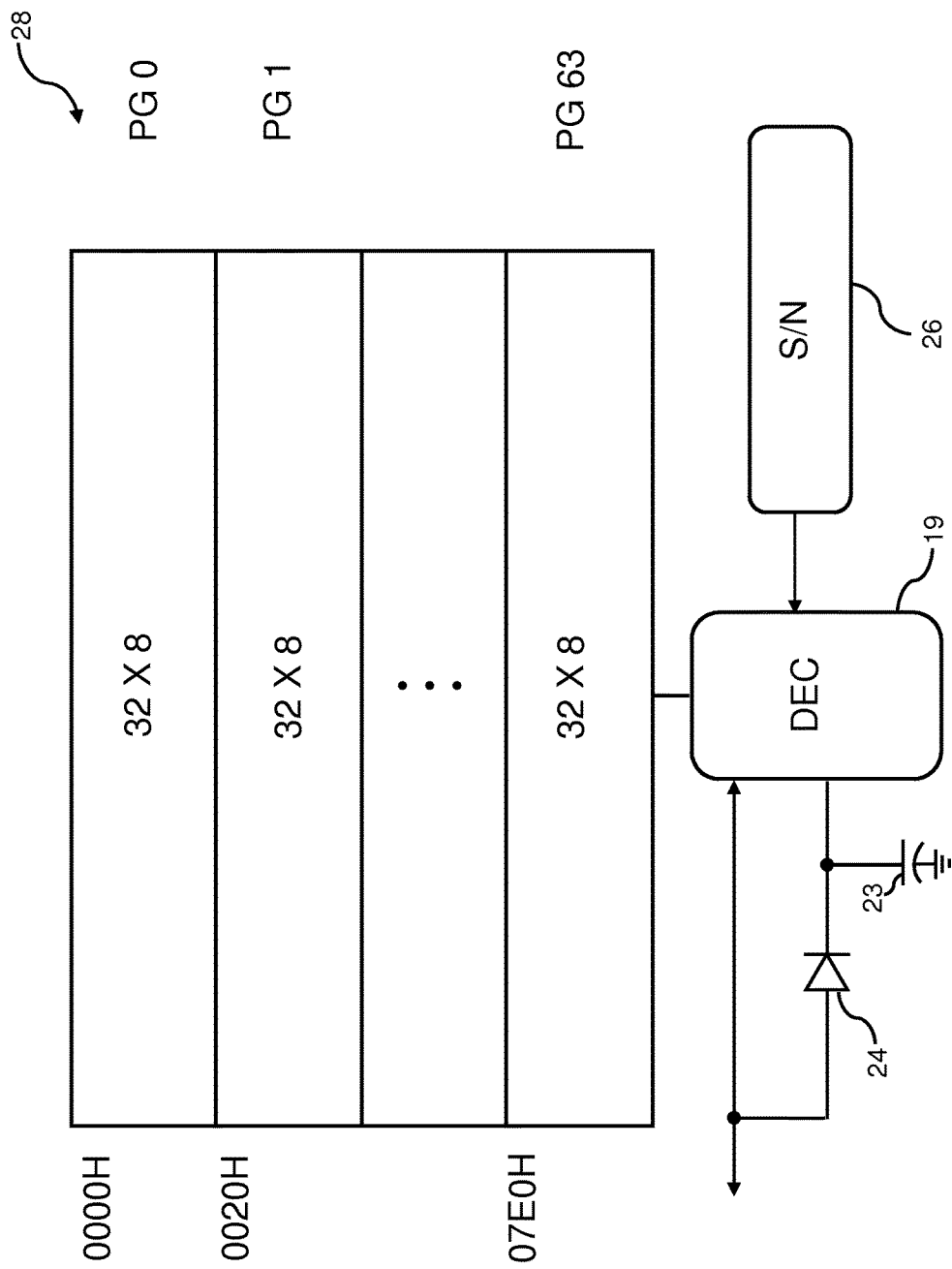
FIG. 8 illustrates a schematic diagram of an exemplary electrical memory device employed in an exemplary robotic device of the prior art.

Referring to FIG. 8, a schematic diagram of the internals of an exemplary robotic memory device 28 such as one employed in an exemplary robotic device 10 of the prior art is shown. This exemplary device has a single wire interface 22 through which power is parasitically obtained to power the robotic memory device 28 by, for example, a diode 24 and capacitor 23. A decoder 19 receives commands from the single wire interface 22 and performs the requested operation (e.g., reading or writing to the memory pages, or reading the preprogrammed, unique serial number 26). Many such devices are programmable by increasing the voltage potential from the single wire interface 22 to a voltage greater than that for a logic one value. This higher voltage is used to charge-pump a junction capacitor of a high impedance field-effect transistor at the selected bit address, thereby changing that bit's logic value (from one to zero or zero to one). Many such devices do not have internal logic to bleed off this charge once it is made and, therefore, do not permit changing the logic value back once it is written, therefore, the memory is basically write once.

Figure 9:
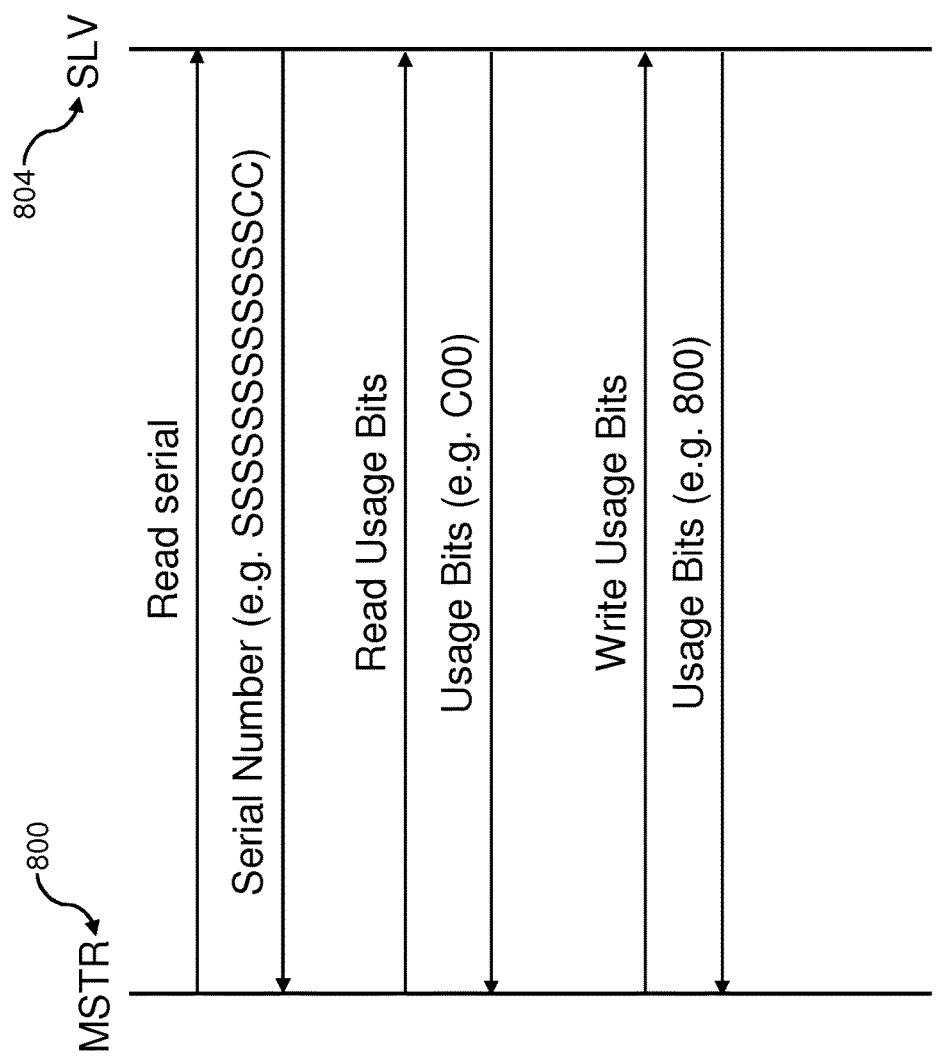
FIG. 9 illustrates a schematic diagram of an exemplary handshake employed between an exemplary robotic control system of the prior art and an exemplary robotic device of the prior art.

Referring to FIG. 9, a schematic diagram of an exemplary handshake employed between an exemplary robotic control system 70 of the prior art and an exemplary robotic device 10 of the prior art is shown. In this example, the master 800 (left side) is the robotic control system 70 and the slave 804 (right side) is the robotic memory device 28. Based upon the device protocol for the robotic memory device 28, the master sends a set of bits indicating that the master is requesting the unique serial number (SSSSSSSSSSSSCC) of the robotic memory device 28 or a serial number stored within the robotic memory device 28. The command is sent one bit at a time using a communication protocol established between the master 800 and the slave 804, for example, a protocol specified for the robotic memory device 28. Once the command is received, decoded, and verified by the existing robotic memory device 28, the robotic memory device 28 (slave) reads the serial number from memory or other internal registers and sends back a response to the master 800, again, one bit at a time based upon the established protocol.

Now, assume the master has just verified the serial number (e.g., through a CRC code) and now needs to determine if the robotic device 10 can be used (e.g., has not exceeded a usage threshold determined by the manufacturer). Again, based upon the device protocol for the robotic memory device 28, the master 800 sends a set of bits indicating that the master 800 is requesting a read of the bit registers representing prior usage counts from the robotic memory device 28. The read command is sent one bit at a time using the communication protocol established between the master 800 and the slave 804, for example, the protocol specified for use with the robotic memory device 28. Once the command is received, decoded, and verified by the robotic memory device 28, the robotic memory device 28 (slave 804) reads the bit registers representing prior usage (e.g., 0F) from memory or other internal registers and sends back a response to the master 800, again, one bit at a time based upon the established protocol.

If the robotic control system 70 determines that the robotic device 10 can be used (e.g., has not exceeded a usage threshold determined by the manufacturer), the robotic control system commands the robotic memory device 28 to write back a modified set of bits indicating one less usage is available. Again, based upon the device protocol for the robotic memory device 28, the master 800 sends a set of bits indicating that the master 800 is requesting a write of the bit registers representing prior usage counts to the robotic memory device 28. The write command and new bit values is sent one bit at a time using the communication protocol established between the master 800 and the slave 804, for example, the protocol implemented by the robotic memory device 28. Once the command and new values is received, decoded, and verified by the robotic memory device 28, the robotic memory device 28 (slave 804) writes the requested values to the internal bit registers representing prior usage (e.g., 07) of the robotic memory device 28 (or other internal register) and sends back a response to the master 800 indicating status (e.g., success), again, one bit at a time based upon the established protocol. In this example, the initial usage bits read were CC0 (110011000000) indicating that four uses remain. The new value written is C80 (110010000000) indicating that three uses remain.

After the last allowed use of the robotic device 10, the new value written is, for example, 0 (all bits are zero). A subsequent attempt to use this robotic device 10 results in the read operation returning all zeros and the robotic control system (master 800), consequently reports that this robotic device 10 is no longer capable of being used, at which time, a new robotic device 10 must be used.

Once the usage bits indicate that the robotic device 10 is no longer usable, instead of disposing of the robotic device 10, the robotic device 10 is refurbished. It is envisioned that a refurbishing operation is performed on the robotic device including any required cleaning, lubricating, replacement of components that may wear out such as seals, etc., and, perhaps sharpening or replacing of blades, etc. Unfortunately, with the usage bits being expired, even after refurbishment, such a robotic device 10 will still not operate, being that the robotic device control system 70 will still read the usage data from the robotic memory device 28 and determine that the device cannot be used. To get around this artificial device limitation, during the refurbishment process, the interceptor 32 is installed within the robotic device 10 by, for example by disconnecting leads of the existing interface 20 on the circuit board 21 and connecting the paths/leads to the interceptor 32.

Once in place, as described in FIG. 10, the interceptor 32 prevents the robotic device control system 70 from believing that such robotic device 10 is no longer usable, by a predetermined, programmed number of uses.

Figure 10A:
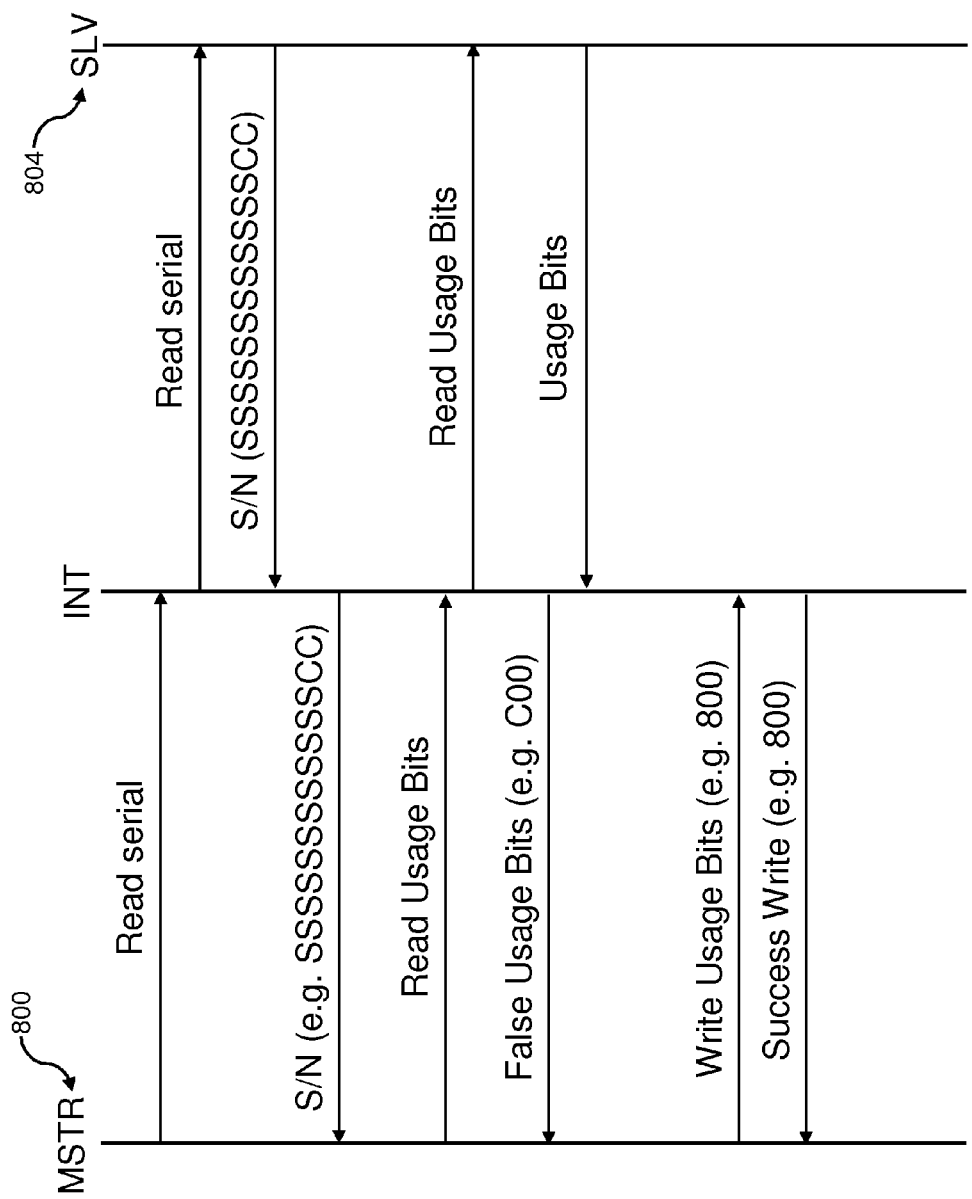
FIGS. 10A, 10B, and 10C illustrate schematic diagrams of an exemplary handshake employed between an exemplary robotic control system of the prior art and the interceptor system, along with exemplary handshake employed between the interceptor system and an exemplary robotic device of the prior art.
Figure 10B:
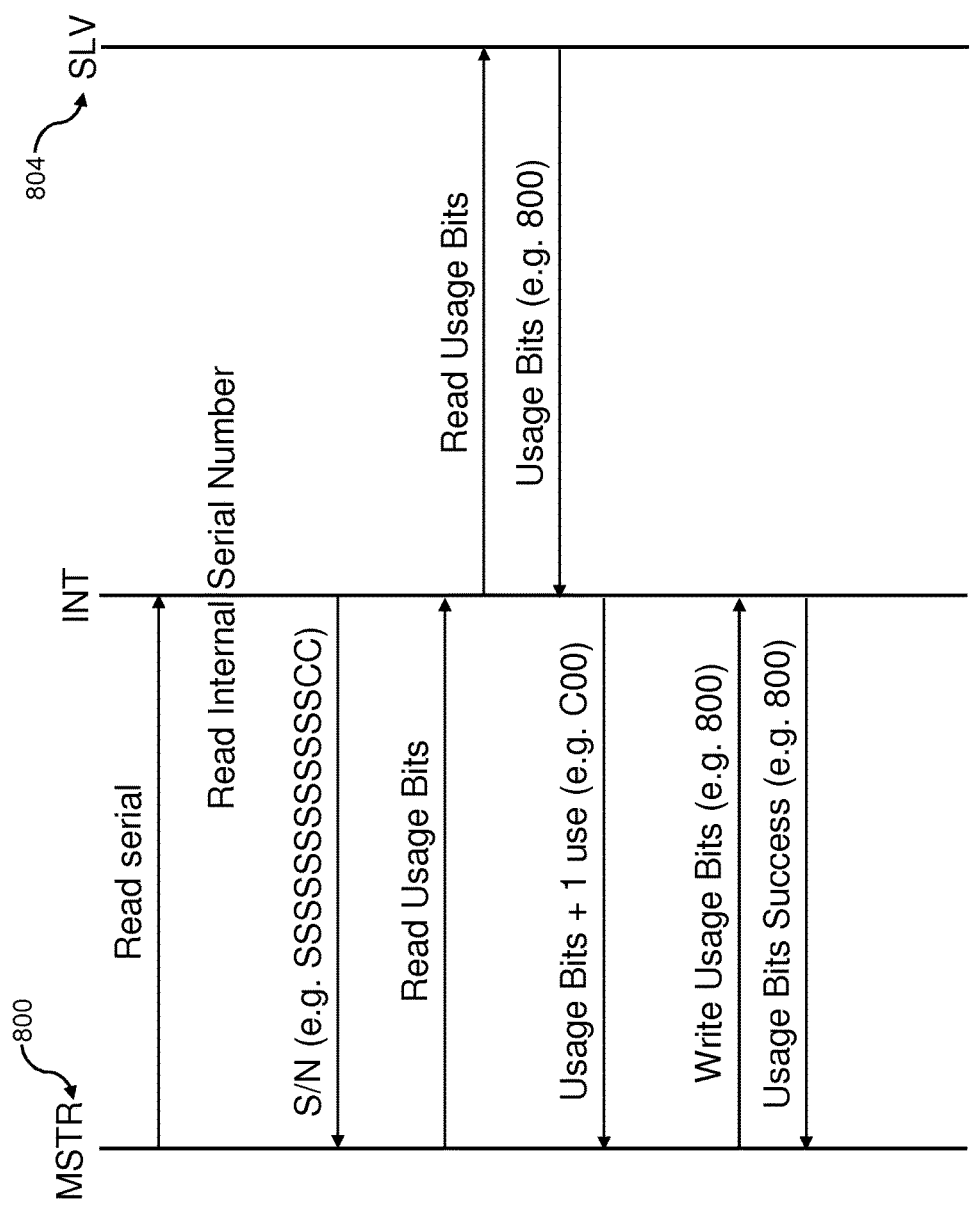
Figure 10C:
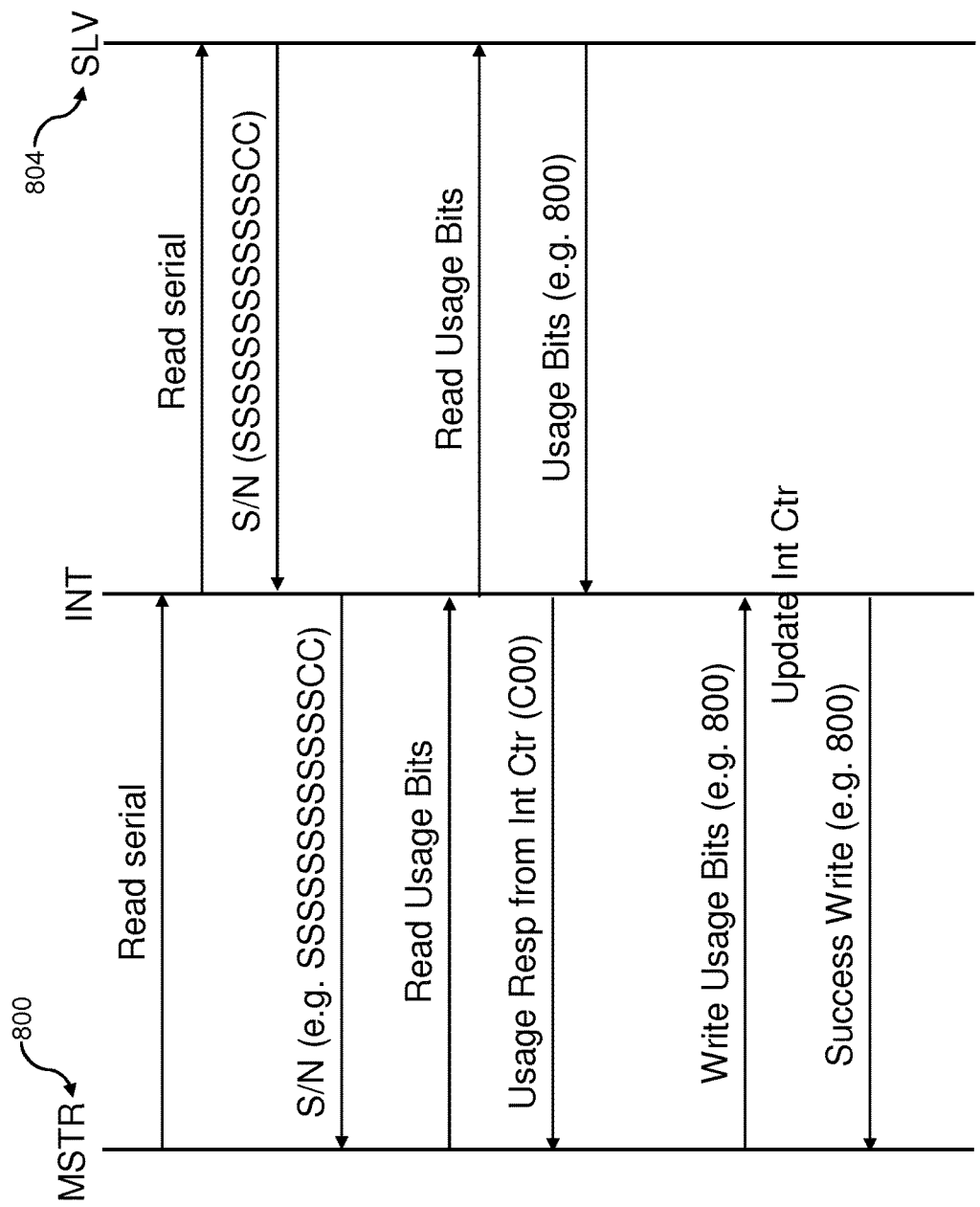

Referring to FIGS. 10A, 10B, and 10C, schematic diagrams of an exemplary handshake employed between an exemplary robotic control system 70 and the interceptor 32, along with exemplary handshake employed between the interceptor 32 and an exemplary robotic device 10 is shown. In this example, the master 800 (left side) is the robotic control system 70, the slave 804 (right side) is the robotic memory device 28, and the interceptor 32 is interfaced between the robotic control system 70 and the robotic memory device 28.

In this modified system, based upon the device protocol for the existing interface 20, the master 800 sends a set of bits indicating that the master 800 is requesting a reading of the unique serial number (SSSSSSSSSSSSCC) of the robotic memory device 28 or a serial number stored within the robotic memory device 28. The command is sent one bit at a time using a communication protocol established between the master 800 and the interceptor 32, for example, a protocol specified for the robotic memory device 28.

In the embodiments of FIGS. 10A and 10C, once the command is received, decoded, and verified as a "read serial number" command by the interceptor 32, the interceptor 32 forwards the command to the robotic memory device 28. The robotic memory device 28 (slave 804) reads the serial number from memory or other internal registers and sends back a response to the interceptor 32 and the interceptor 32 forwards the response to the master 800, again, one bit at a time based upon the established protocol. In the embodiment of FIG. 10B, once the command is received, decoded, and verified as a "read serial number" command by the interceptor 32, the interceptor 32 prevents the command from getting to the robotic memory device 28. Instead, the interceptor 32 reads an internal serial number from local interceptor memory 33 and sends back a response to the master 800 including this internal serial number, again, one bit at a time based upon the established protocol. In some embodiments, the interceptor 32 forwards the "read serial number" command to the robotic memory device 28, but ignores the response and sends back a response to the master 800 including the internal serial number instead.

Now, assume the master 800 has just verified the serial number (e.g., through a CRC code) and now needs to determine if the robotic device 10 can be used (e.g., has not exceeded a usage threshold determined by the manufacturer). Again, based upon the device protocol for the robotic memory device 28, the master 800 sends a set of bits indicating that the master 800 is requesting a read of the bit registers representing prior usage counts from the robotic memory device 28, believing that the master 800 is communicating with the existing robotic memory device. The read command is sent one bit at a time using the communication protocol established between the master and the interceptor 32, for example, the protocol specified for the robotic memory device 28. Once the command is received, verified, and decoded as a "read usage data" command by the interceptor 32, the interceptor 32 (e.g., logic within the logic array 32) prepares a response without forwarding the command to the robotic memory device 28 (or in some embodiments, forwarding the command to the robotic memory device 28 but ignoring the response). There are many ways to respond with a valid set of usage data depending upon what will be accepted by the control system 79. For example, the interceptor 32 responds with data indicating that one usage remains (e.g., one bit is set) or the interceptor 32 reads the current usage data from the robotic memory device 28 (through the single wire protocol between the logic array 32 and the robotic memory device 28) and amends the value to include one additional usage, etc. In FIG. 10A the usage bits are not read from the slave 804 and a programmed usage count (e.g., a constant value) is provided to indicate to the master that at least one additional use is available (e.g., 800). In FIG. 10B, the usage bits are read from the slave 804 (e.g., 000 in this example meaning that no further uses are available) and this value is amended to include one additional use is available (e.g. 800). In embodiments in which the interceptor 32 includes interceptor memory 33 in which an internal usage counter is stored, the internal usage counter is read by the interceptor 32 and a usage response is sent back to the maser 800 containing the value from the internal counter, encoded as expected by the master 800, as shown in FIG. 10C.

If there is an indication that at least one use remains, the robotic control system 70 determines that the robotic device 10 can be used (e.g., has not exceeded a usage threshold determined by the manufacturer). At some time later, the robotic control system 70 commands the robotic device 10 to write back a modified set of bits indicating one less usage is available, which is intercepted by the interceptor 32. In such, the master 800 sends a set of bits indicating that the master 800 is requesting a write of the bit registers representing usage counts, believing that the request will modify the robotic memory device 28. The write command and new bit values is sent one bit at a time using the communication protocol established, for example, the protocol specified for the robotic memory device 28. Once the command and new values is received, decoded, and verified by the interceptor 32, in the examples of FIGS. 10A and 10B, the interceptor 32 sends back a response to the master indicating status (e.g., success), again, one bit at a time based upon the established protocol, even though no data was written. In some embodiments, the interceptor 32 must determine a proper response or the robotic control system 70 will indicate a fault with the robotic device 10. The actual usage data within the robotic memory device 28 are not modified.

In the embodiment of FIG. 10C, an internal usage counter stored within the interceptor memory 33 is set to the new value that was received in the write transaction (assumed to be one less than the previously stored value) and a response is sent to mimic a successful response from the robotic memory device 28. In this way, during refurbishment, the internal usage counter stored within the interceptor memory 33 is set to a predetermined value (e.g., ten uses), then after the control system 70 reads this value (ten), and later (after use), the control system 70 writes a new value of nine, the new value is then stored in the internal usage counter within the interceptor memory 33 by the interceptor 32 so that, the next time the control system 70 reads the usage data, the new value (e.g., nine), is read from the internal usage counter within the interceptor memory 33 and transmitted back to the control system 70, and so on. It is therefore envisioned that, during the refurbishment process, the internal usage counter within the interceptor memory 33 is set to any valid number of uses as determined by the refurbishment process. For example, if the refurbishment process includes components that are expected to last for eight uses, then during the refurbishment process, the internal usage counter within the interceptor memory 33 is set to eight, such that, after eight more uses, the robotic device 10 is no longer recognized by the control system 70 and must be again refurbished. Note that although the internal interceptor memory 33 is likely capable of storing usage count values higher than originally anticipated by the manufacturer, it is anticipated that in some protocols, there is no way to communicate such higher values back to the control system 70. For example, if the representation of the usage count includes ten bit positions in the response protocol, a one in any of the positions indicating a remaining use is possible, there is no way to respond to the control system 70 indicating that there are eleven uses remaining, etc. Further, even if the protocols do provide for communicating of higher usage counts back to the control system 70, in some such control systems 70 the operation software is incapable of properly displaying higher usage counts due to programming limitations, etc.

Figure 11:
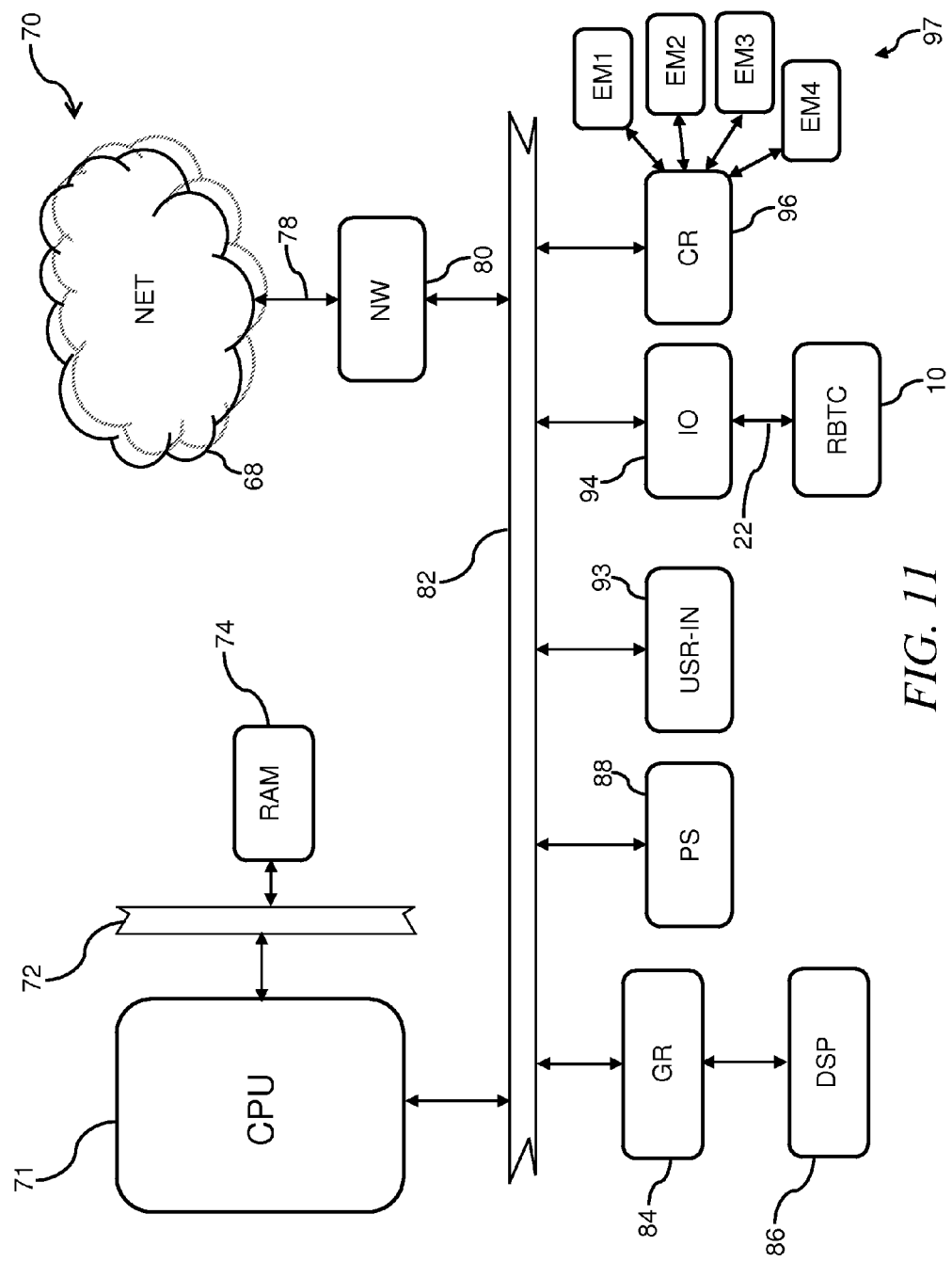
FIG. 11 illustrates a schematic view of a typical computer system, as used in a robotic control system.

Referring to FIG. 11, a schematic view of a typical robotic device control system 70 is shown. The exemplary robotic device control system 70 represents a typical robotic device control system used in many surgical procedures. This exemplary robotic device control system 70 is shown in its simplest form. Different architectures are known that accomplish similar results in a similar fashion and the present invention is not limited in any way to any particular robotic device control system 70 architecture or implementation. In this exemplary robotic device control system 70, a processor 71 executes or runs programs from a memory 74. The programs that control the robotic devices 10 are generally loaded into the random access memory 74 when needed. The processor 71 is any processor, suited for controlling robotic devices 10. The random access memory 74 is typically connected to the processor 71 by, for example, a memory bus 72. The random access memory 74 is any memory 74 suitable for connection and operation with the selected processor 71, such as SRAM, DRAM, SDRAM, RDRAM, DDR, DDR-2, etc.

Also connected to the processor 71 is a system bus 82 for interfacing with peripheral subsystems such as a network interface 80 and a graphics adapter 84. The graphics adapter 84 receives commands from the processor 70 and controls what is depicted on a display image on the display 86, including images of the robotic device 10 in operation, status of the system and robotic device 10, etc.

In general, persistent storage 88 stores operating procedures, control data, programs, etc., as known in the industry.

The peripherals shown are examples and other peripherals are known in the industry such as speakers, microphones, USB interfaces, Bluetooth transceivers, Wi-Fi transceivers, image sensors, temperature sensors, etc., the likes of which are not shown for brevity and clarity reasons.

The network interface 80 connects the robotic device control system 70 to other systems for various purposes such as updating software, downloading of data such as X-rays and patient records, collaboration with other surgeons, etc.

The control system 70 communicates with the robotic device(s) 10 through a communication system, shown as an I/O port 94. Many different communication systems are anticipated and the simplified I/O port 94 is one example using any form of data communication to the robotic device 10, including, but not limited to any of the various known digital and analog interfaces such as NRZ (non-return to zero), RS-232, I2C, IIC, etc. In some embodiments, a wireless interface such as near-field or Bluetooth is also anticipated.

In the examples shown, electrical signals from the I/O port 94 communicate with a receiving device associated with the robotic device 10 over a single-wire interface 22 based upon a protocol devised by the manufacturer of the robotic device control system 70 and/or memory device 20/28.

Various operations and activities are controlled through electro-mechanical mechanisms 97 within the robotic device control system 70. For example, an electromechanical device 97 associated with the control system, 70 rotates a hub 20 degrees, the hub being coupled to a wheel within the robotic device 10, resulting in a particular movement of an instrument 16 at the end of an arm of the robotic device 10. In such, the robotic device control system 70 has one or more electromechanical devices 97 that are electrically controlled by a control interface 96, as known in the industry.

Robotic device control systems 70 typically have one or more user controls 93 such as foot pedals, keyboards, joysticks, mice, etc., through which the surgeon typically maneuvers to effect a specific movement or operation of the instrument at the end of the robotic device 10.

Figure 12:
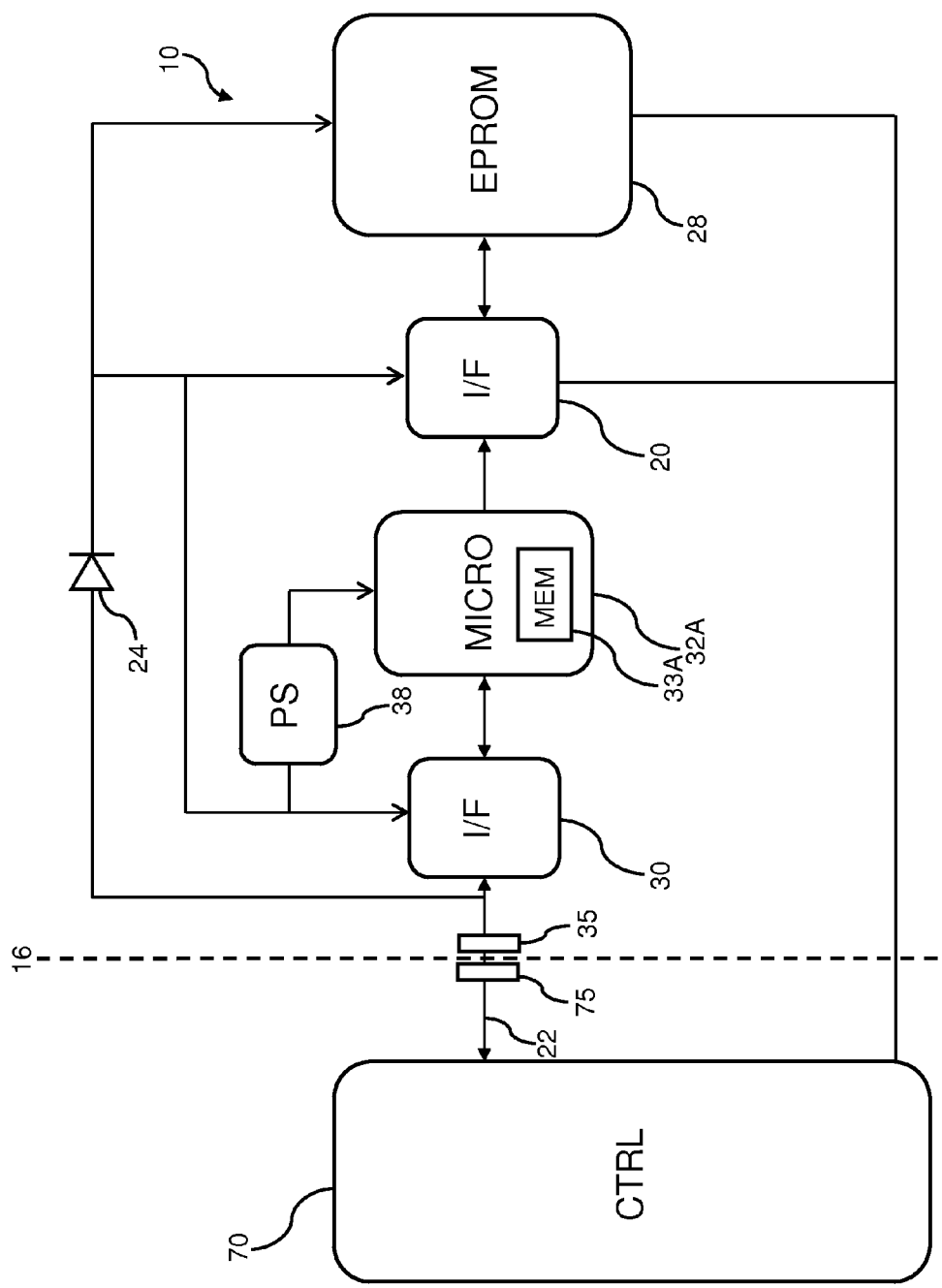
FIG. 12 illustrates a schematic view of exemplary electrical arrangements between an exemplary robotic control system of the prior art and an exemplary robotic device modified with an interceptor system using a processor.

Referring to FIG. 12, a schematic view of an exemplary electrical arrangement between an exemplary robotic control system 70 of the prior art and an exemplary robotic device 10 modified with a processor-based interceptor system is 32A is shown. As described previously, the exemplary interface uses a single wire interface 22 to communicate with the control system 70. In this exemplary robotic device 10, the robotic memory device 28 receives control protocol commands from an interceptor 32A (processor based) instead of from the control system 70. In other words, a processor-based interceptor 32A is inserted between the control system 70 and robotic memory device 28.

The robotic memory device 28 (e.g., EPROM) reports back results to the interceptor 32A through the same protocol over the single wire interface 22. The control system 70 believes that it is communicating directly with the robotic memory device 28 through the single wire interface 22, but instead, is communicating with the interceptor 32A.

The interceptor 32A optionally has interfaces 20/30 for receiving and responding to commands to/from the robotic control system 70 and to/from the robotic memory device 28. In this embodiment, the interceptor 32A is a processor 32A that makes decisions regarding commands sent from the control system 70. For example, most commands for reading the robotic memory device 28 are received by the logic array 32 and processed by forwarding the exact command to the robotic memory device 28. The interceptor 32A intercepts certain requests, an example of which is described later along with FIGS. 13A and 13B.

Note that any processor is anticipated; especially very low power single chip processors as known in the industry.

Figure 13A:
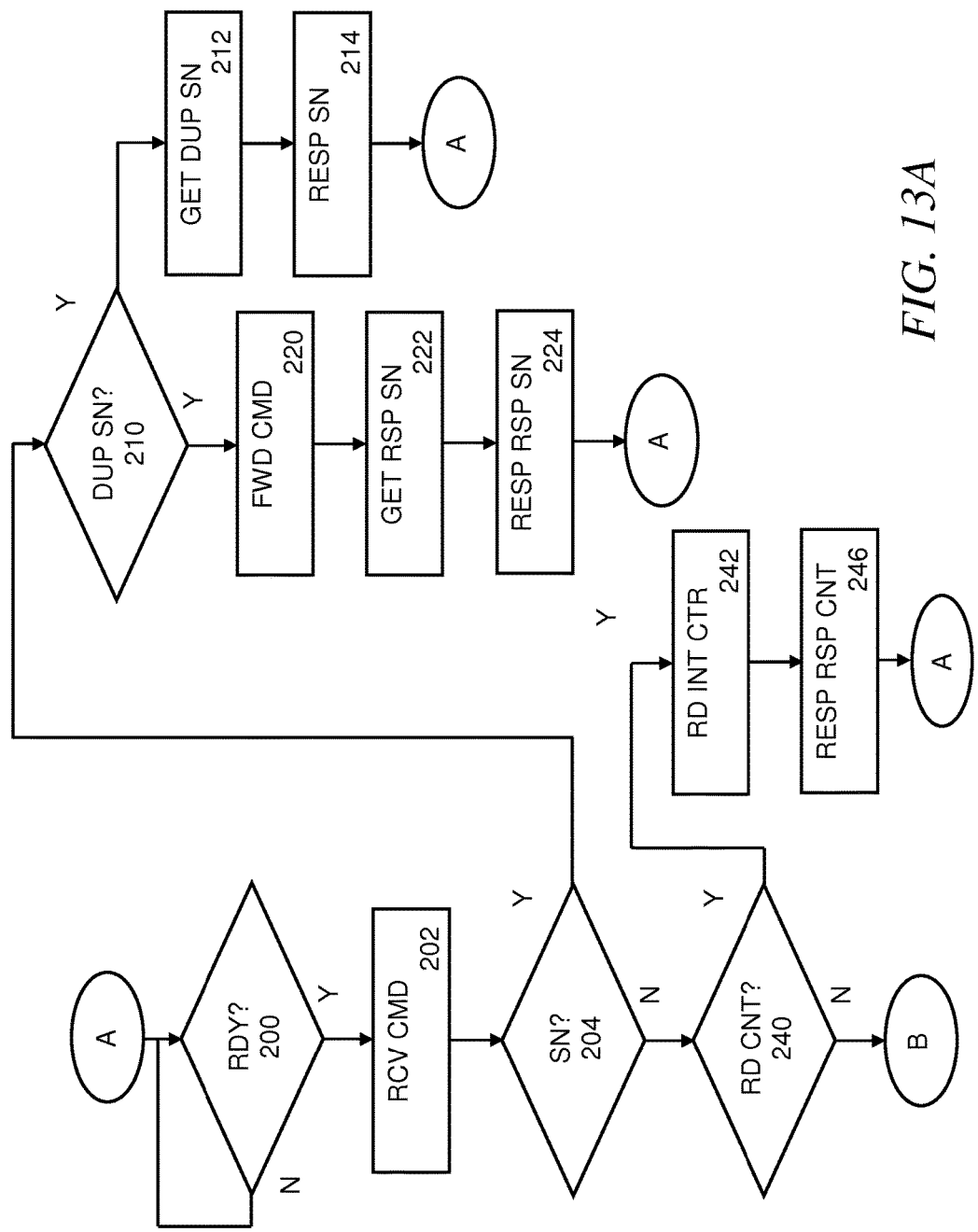
FIGS. 13A and 13B illustrate schematic views of an exemplary software flowchart implementing the interceptor system.
Figure 13B:
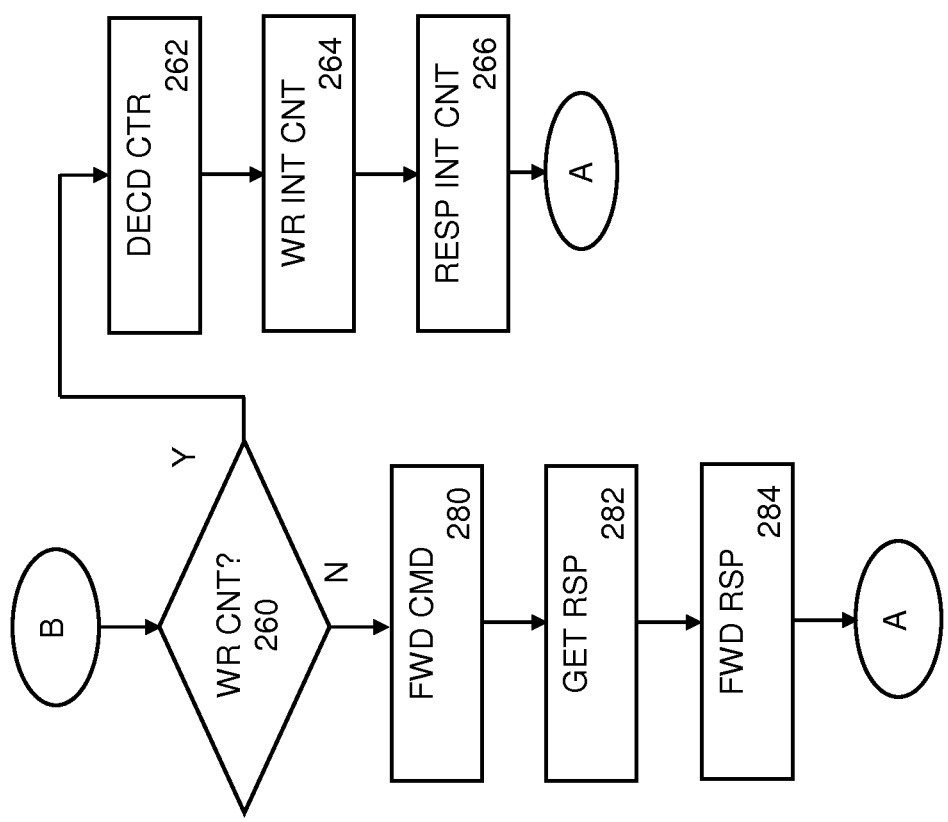

Referring to FIGS. 13A and 13B, schematic views of an exemplary software flowchart implementing the interceptor system is shown. As it is known in the industry, logic such as that implemented by a logic array 32 is often implemented by software executed by a processor-based interceptor 32A and vice versa. Therefore, an exemplary flow is shown in FIGS. 13A and 13B describing how an embodiment of the disclosed functionality is implemented in software instead of in a logic array 32.

In the exemplary flow of FIGS. 13A and 13B, the software waits 200 for an initial signal from the control system 70, the interceptor 32 (processor based in this embodiment) receives a command 202 which, in some cases, includes an address or data (e.g., set address to <value> or write data <value> to the current address). If the command is a request to read the serial number 204 (some robotic memory devices 28 include a laser-set unique serial number or a serial number is stored in the robotic memory device 28), the software determines 210 if the serial number from the existing robotic memory device 28 is to be returned or if a generated serial number is to be returned. This determination is made, for example, by reading a flag set in interceptor memory 33A or reading interceptor memory 33A to see if it has been loaded with a generated serial number during initialization. If the software determines 210 that a generated serial number is to be returned, the software loads the generated serial number 212 and responds 214, providing the generated serial number as expected by the robotic control system 70 (e.g., using the established protocol over the single wire interface 22). If the software determines 210 that the real serial number is to be returned, the software forwards 220 the "read serial number" command to the robotic memory device 28. After/while the robotic memory device 28 responds 222 to the software with the real serial number, the software forwards the response 224 (e.g., real serial number) to the control system 70, providing the real serial number as expected by the robotic control system 70 (e.g., using the established protocol over the single wire interface 22). Note that, in some embodiments, the response is buffered (e.g., received in entirety) before forwarding 224 to the control system 70 while in some embodiments, each bit received from the robotic memory device 28 is forwarded 224 directly to the control system 70, as it is received.

If the command received from the control system 70 is not a request to read the serial number 204, the software determines if the command is a read remaining uses count 240, in which case, the software reads 242 the internal use counter (e.g., stored in interceptor memory 33A) and responds 246 to the control system 70 with a bit stream that has the current value of the internal use counter embedded as expected by the control system 70. In this, the control system 70 is actually reading a number of remaining uses from the interceptor memory 33A of the interceptor 32A, rather than from the robotic memory device 28.

If the command received from the control system 70 is not a request to read the remaining uses count 240, the software determines if the command is a "write remaining uses count" 260, in which case, the software decodes 262 the data received from the control system 70 to match an internal representation of the remaining uses count and then writes 264 the remaining uses count to the internal remaining uses counter in the interceptor memory 33A. At this point, in some embodiments, the software simulates the robotic memory device 28 by implementing steps to assure that proper writing operations are performed, for example, if the robotic memory device 28 only permits writing bit values from one to zero (not from zero to one), then the software simulates this logic operation while writing to the internal remaining uses counter. The software then responds 266 to the control system 70 with a bit stream that is encoded as expected by the control system 70. In this, the control system 70 is actually writing a number of remaining uses to the interceptor, rather than to the robotic memory device 28.

If the command received from the control system 70 is not a request to "write the remaining uses count" 260 (e.g., the request is other than "read serial number," "read usage counter," or "write usage counter"), the software forwards 280 the command to the robotic memory device 28. After/while the robotic memory device 28 responds 282 to the software, the software forwards 284 the response (e.g., data, status, etc.) to the control system 70, providing the response as expected by the robotic control system 70 (e.g., using the established protocol over the single wire interface 22). Note that, in some embodiments, the response is buffered (e.g., received in entirety) before forwarding 284 to the control system 70 while in some embodiments, each bit received from the robotic memory device 28 is forwarded 284 directly to the control system 70, as it is received.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A device for extending the life of a robotically controlled device, the robotically controlled device connectable to a control system through an interface, the interface including an electrical interface for connecting the system to a robotically controlled device-based circuit, the device for extending the life of a robotically controlled device comprising:
    a circuit inserted in the electrical interface for communicating with the control system, the circuit intercepts requests from the control system such that the circuit recognizes at least one of the requests and the circuit responds to the at least one of the requests; and requests other than the at least one of the requests are received by the robotically controlled device-based circuit of which a response from the robotically controlled device-based circuit is received by the control system;
    whereas the control system properly recognizes the robotically controlled device after the circuit is inserted;
    wherein the circuit includes memory for maintaining internal usage data; a first one of the at least one of the requests is a request to read usage data from the robotically controlled device-based circuit; and whereas after the circuit recognizes the request to read the usage data, the circuit reads the internal usage data from the memory and the circuit responds to the control system with a response that includes the internal usage data that was read from the memory.

2. The device for extending the life of the robotically controlled device of claim 1, wherein the circuit includes logic that recognizes the at least one of the requests and the logic formats and sends a response for the at least one request to the control system.

3. The device for extending the life of the robotically controlled device of claim 2, wherein the logic is within a logic array.

4. The device for extending the life of the robotically controlled device of claim 1, wherein the circuit includes software executing on a processor, the software recognizes the at least one of the requests and the software formats and sends a response for the at least one request to the control system.

5. The device for extending the life of the robotically controlled device of claim 1, wherein a second one of the at least one of the requests is a request to write a value to the usage data; and after the circuit recognizes the request to write the usage data, the circuit writes the value to the internal usage data of the memory and the circuit responds to the control system with a response that acknowledges success.

6. The device for extending the life of the robotically controlled device of claim 1, wherein the interface is a single wire interface.

7. The device for extending the life of the robotically controlled device of claim 6, whereas power for the circuit is derived from the single wire interface.

8. A method of refurbishing a robotically controlled device, the robotically controlled device comprising an interface for communicating between a control system and a robotically controlled device-based circuit for storing data associated with the robotically controlled device, the robotically controlled device-based circuit is physically interfaced to the robotically controlled device, the robotically controlled device-based circuit is electrically connected to the control system through one or more conductors, the method comprising:
    disconnecting at least one of the one or more conductors into two sets of one or more conductors, a first set of one or more conductors of the two sets of one or more conductors for communicating with the control system and a second set of one or more conductors of the two sets of one or more conductors for communicating with the robotically controlled device-based circuit; and
    inserting a circuit having a first interface connected to the first set of one or more conductors and a second interface connected to the second set of one or more conductors, the circuit recognizes at least one request from the first interface and the circuit responding directly to the at least one requests; the circuit forwarding at least one other request from the first interface to the second interface and the circuit forwarding a response from second interface back to the first interface;
    wherein the circuit includes memory for maintaining internal usage data; a first one of the at least one requests is a request to read usage data from the robotically controlled device-based circuit; and whereas after recognizing the request to read the usage data by the circuit, the method includes the steps of reading the internal usage data from the memory by the circuit, formatting a response that includes the internal usage data that was read from the memory by the circuit, and sending the response on the first interface by the circuit.

9. The method of claim 8, further comprising any of the steps comprising inspecting the robotically controlled device, replacing worn parts on the robotically controlled device, and lubricating the robotically controlled device.

10. The method of claim 8, wherein the circuit includes logic, the logic recognizing the at least one request, the logic formatting a response to the at least one request, and the logic sending the response through the first interface.

11. The method of claim 10, wherein the logic comprises a logic array.

12. The method of claim 10, wherein a second one of the at least one of the requests is a request to write a value to the usage data; and after recognizing the request to write the usage data by the circuit, the method further comprising writing the value into the internal usage data of the memory by the circuit, and responding to the request to write the usage data by the circuit over the first interface with a response that indicates success.

13. The method of claim 8, wherein the interface is a single wire interface.

14. A device for extending the life of a robotically controlled device, the robotically controlled device having an electrical interface for communicating between a control system and a robotically controlled device-based circuit mounted within the robotically controlled device, the device for extending the life of the robotically controlled device comprising:
    a circuit is connected to the electrical interface, the circuit having a logic array, the logic array intercepts requests from the electrical interface such that the logic array recognizes at least one request from the control system and the logic array responds to the at least one request by sending a response to the control system over the electrical interface; and at least one other request is forwarded by the logic array to the robotically controlled device-based circuit of which a response from the robotically controlled device-based circuit is received by the logic array and the response is forwarded by the logic array to the control system over the electrical interface;
    wherein the logic array includes memory for maintaining internal usage data; a first one of the at least one request is a request to read usage data from the robotically controlled device-based circuit; and whereas after the logic array recognizes the request to read the usage data, the logic array reads the internal usage data from the memory and the logic array responds to the control system over the electrical interface with a response that includes the internal usage data that was read from the memory.

15. The device for extending the life of the robotically controlled device of claim 14, wherein a second one of the at least one request is a request to write a value to the usage data, and after the logic array recognizes the request to write, the logic array writes the value to the internal usage data in the memory and the logic array responds over the electrical interface with a response that indicates success.

16. The device for extending the life of the robotically controlled device of claim 14, wherein a second one of the at least one request is a request to write a set of usage count bits, each of the usage count bits representing one remaining use; and after the logic array recognizes the request to write the set of usage count bits, the logic array writes a value representing the set of usage count bites to the internal usage data of the memory adhering to an algorithm in which the usage count bits in the internal usage data cannot be changed from a zero to a one and therefore, the set of usage count bits stored in the memory is not increased, the logic array then responds over the electrical interface with a response that indicates success.

17. The device for extending the life of the robotically controlled device of claim 14, whereas power for the circuit is derived from the electrical interface.

\* \* \* \* \*